US010485562B2

(12) United States Patent
Luo et al.

(10) Patent No.: US 10,485,562 B2
(45) Date of Patent: Nov. 26, 2019

(54) POSITIONING DEVICE FOR SECURING AN INTRAMEDULLARY NAIL IN A LONG BONE

(71) Applicant: OT MEDIZINTECHNIK GMBH, München (DE)

(72) Inventors: Hao Luo, Hefei (CN); Ulrich Schreiber, München (DE)

(73) Assignee: OT MEDIZINTECHNIK GMBH, Munich (DE)

(*) Notice: Subject to any disclaimer, the term of this patent is extended or adjusted under 35 U.S.C. 154(b) by 0 days.

(21) Appl. No.: 15/326,637

(22) PCT Filed: Jul. 13, 2015

(86) PCT No.: PCT/EP2015/065977
§ 371 (c)(1),
(2) Date: Jan. 16, 2017

(87) PCT Pub. No.: WO2016/008849
PCT Pub. Date: Jan. 21, 2016

(65) Prior Publication Data
US 2017/0202566 A1  Jul. 20, 2017

(30) Foreign Application Priority Data
Jul. 15, 2014 (DE) .................. 10 2014 109 935
Apr. 7, 2015 (DE) .................. 10 2015 105 242

(51) Int. Cl.
A61B 17/72 (2006.01)
A61B 17/17 (2006.01)
(Continued)

(52) U.S. Cl.
CPC .......... A61B 17/1725 (2013.01); A61B 17/72 (2013.01); A61B 17/8872 (2013.01);
(Continued)

(58) Field of Classification Search
CPC ............................................ A61B 17/72–7283
See application file for complete search history.

(56) References Cited

U.S. PATENT DOCUMENTS 4,875,475 A * 10/1989 Comte ............... A61B 17/7225
606/64
5,433,720 A * 7/1995 Faccioli ............. A61B 17/1707
606/87
(Continued)

FOREIGN PATENT DOCUMENTS

AT  507 086 B1   2/2010
DE  101 10 246 A1  10/2002
(Continued)

OTHER PUBLICATIONS

PCT/EP2015/065977, International Search Report, dated Oct. 12, 2015, European Patent Office.
(Continued)

Primary Examiner — Eduardo C Robert
Assistant Examiner — Michelle C Eckman
(74) Attorney, Agent, or Firm — Millman IP Inc.

(57) ABSTRACT

The present invention relates to a positioning device (100, 100', 100") for securing an intramedullary nail (19) in a long bone, said positioning device comprising a guide bow (1), with an adjusting device (3) and a sleeve guide (2), wherein the adjusting device (3) has a targeting device (5); and wherein the targeting device (5) is designed to receive a locking device (21) or an instrument (23) for acting on the locking device (21); and wherein the sleeve guide (2) has a sleeve (7), which sleeve (7) is mounted in the sleeve guide (2) such that it can be rotated and/or slid relative to the sleeve guide (2); and wherein the sleeve (7) has a longitudinal through-opening for receiving a guiding device therein.

20 Claims, 16 Drawing Sheets

(51) Int. Cl.
  *A61B 17/88*  (2006.01)
  *A61B 17/86*  (2006.01)
  *A61B 17/90*  (2006.01)
  *A61B 17/00*  (2006.01)

(52) U.S. Cl.
  CPC .............. *A61B 17/86* (2013.01); *A61B 17/88* (2013.01); *A61B 2017/00477* (2013.01); *A61B 2017/90* (2013.01)

(56) References Cited

U.S. PATENT DOCUMENTS

| | | | | |
|---|---|---|---|---|
| 5,474,561 A * | 12/1995 | Yao | A61B 17/1725 | 606/98 |
| 5,620,449 A * | 4/1997 | Faccioli | A61B 17/1725 | 606/96 |
| 5,766,179 A * | 6/1998 | Faccioli | A61B 17/1725 | 606/96 |
| 6,514,253 B1 * | 2/2003 | Yao | A61B 17/1725 | 128/892 |
| 8,414,584 B2 * | 4/2013 | Brigido | A61B 17/1725 | 606/280 |
| 9,814,499 B2 * | 11/2017 | Buscaglia | A61B 17/7233 | |
| 2003/0097131 A1 * | 5/2003 | Schon | A61B 17/72 | 606/62 |
| 2004/0010252 A1 * | 1/2004 | Zander | A61B 17/1725 | 606/53 |
| 2004/0082959 A1 * | 4/2004 | Hayes | A61B 17/1725 | 606/96 |
| 2004/0138671 A1 * | 7/2004 | Zander | A61B 17/1725 | 606/99 |
| 2007/0276382 A1 * | 11/2007 | Mikhail | A61B 17/1725 | 606/62 |
| 2008/0039857 A1 * | 2/2008 | Giersch | A61B 17/1703 | 606/96 |
| 2008/0221577 A1 * | 9/2008 | Elghazaly | A61B 17/7241 | 606/64 |
| 2008/0264109 A1 * | 10/2008 | Ritchey | A61B 17/1725 | 66/88 |
| 2009/0048598 A1 * | 2/2009 | Ritchey | A61B 17/1725 | 606/57 |
| 2009/0062796 A1 * | 3/2009 | Parks | A61B 17/72 | 606/62 |
| 2009/0299375 A1 * | 12/2009 | Wack | A61B 17/1725 | 606/96 |
| 2009/0326541 A1 * | 12/2009 | Metzinger | A61B 17/1725 | 606/98 |
| 2011/0054473 A1 | 3/2011 | Brigido | | |
| 2011/0213379 A1 * | 9/2011 | Blau | A61B 17/1703 | 606/102 |
| 2012/0130434 A1 * | 5/2012 | Stemniski | A61B 17/15 | 606/300 |
| 2012/0209268 A1 * | 8/2012 | Overes | A61B 17/1725 | 606/62 |
| 2012/0239039 A1 * | 9/2012 | Nardini | A61B 17/1725 | 606/64 |
| 2012/0303037 A1 * | 11/2012 | Overes | A61B 17/1725 | 606/96 |
| 2013/0012948 A1 * | 1/2013 | Thornes | A61B 17/1725 | 606/87 |
| 2013/0046311 A1 * | 2/2013 | Blake | A61B 17/1725 | 606/96 |
| 2013/0085502 A1 * | 4/2013 | Harrold | A61B 17/1725 | 606/96 |
| 2013/0110119 A1 * | 5/2013 | Atkinson | A61B 17/1725 | 606/98 |
| 2013/0172890 A1 * | 7/2013 | Limouze | A61B 17/1725 | 606/62 |
| 2014/0214045 A1 * | 7/2014 | Felder | A61B 17/72 | 606/104 |
| 2014/0364859 A1 * | 12/2014 | Wieland | A61B 17/72 | 606/97 |
| 2015/0157338 A1 * | 6/2015 | Feibel | A61B 17/1775 | 606/96 |
| 2015/0265361 A1 * | 9/2015 | Blau | A61B 17/1703 | 606/67 |
| 2015/0305791 A1 * | 10/2015 | Purohit | A61B 17/72 | 606/96 |
| 2015/0351821 A1 * | 12/2015 | Haidukewych | A61B 17/1725 | 606/96 |
| 2016/0089189 A1 * | 3/2016 | Buscaglia | A61B 17/1725 | 606/64 |
| 2016/0199108 A1 * | 7/2016 | Matsuda | A61B 17/846 | 606/62 |
| 2016/0354156 A1 * | 12/2016 | Blau | A61B 17/1725 | |
| 2017/0007303 A1 * | 1/2017 | Hansson | A61B 17/1721 | |
| 2017/0215896 A1 * | 8/2017 | Stemniski | A61B 17/1775 | |

FOREIGN PATENT DOCUMENTS

| | | |
|---|---|---|
| DE | 202 16 857 U1 | 3/2003 |
| DE | 20 2004 014226 U1 | 12/2004 |
| DE | 10 2008 014 697 A1 | 9/2009 |
| EP | 1 759 643 A1 | 3/2007 |
| JP | 2003275219 A | 9/2003 |
| WO | 2005092219 A1 | 6/2005 |
| WO | 2006091625 A2 | 8/2006 |
| WO | 2013120034 A1 | 8/2013 |

OTHER PUBLICATIONS

Office Action for EP Patent Application No. 15738062.7 dated Jun. 8, 2018 (reasons pages translated).

* cited by examiner

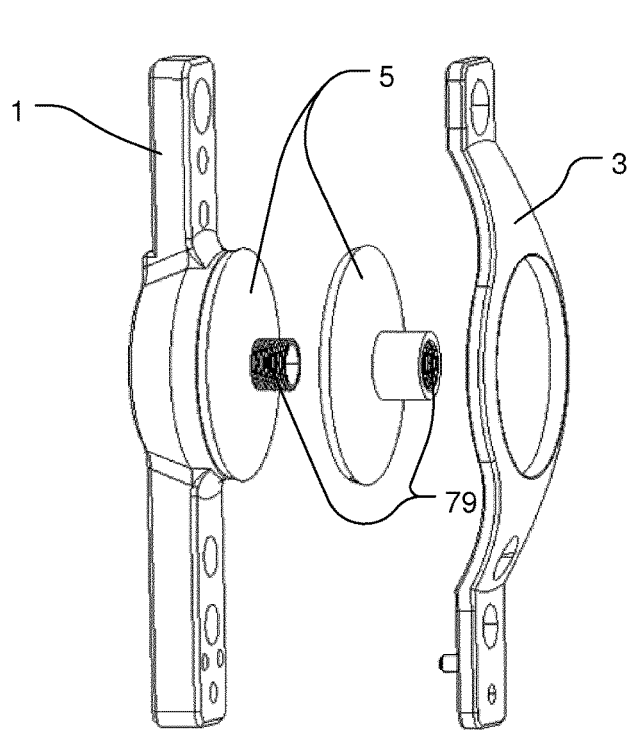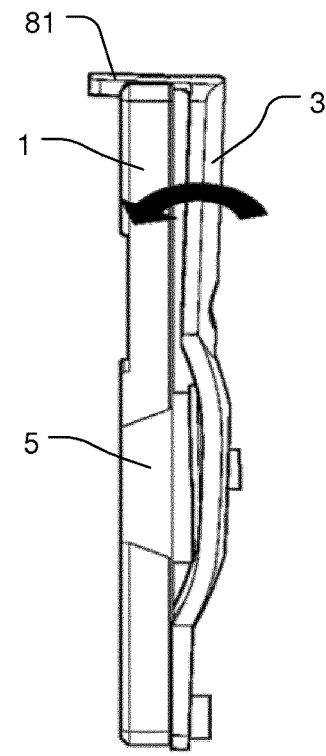
Fig. 19          Fig. 20
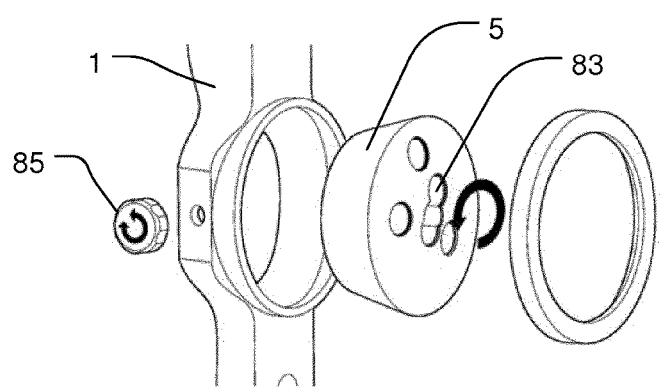
Fig. 21

POSITIONING DEVICE FOR SECURING AN INTRAMEDULLARY NAIL IN A LONG BONE

The present invention relates to a positioning device for securing an intramedullary nail in a long bone according to claim 1.

Intramedullary nails are known aids for the care of fractures of long bones. They are inserted into the intramedullary cavity of the fractured bone in order to mechanically bridge the bone fracture. Intramedullary nail may be designed as so-called interlocking intramedullary nails. In the latter, interlocking screws serve to secure the connection between the bone and the interlocking intramedullary nail against displacement.

So far in the case of known interlocking intramedullary nails, the interlocking screws are placed in the bone in discrete openings of the intramedullary nail in a predetermined position relative to the intramedullary nail. The exact positioning of the interlocking screws in the intramedullary nail, arranged in the long bone, requires a great experience of the surgeon when inserting the intramedullary nail into the bone.

It is an object of the present invention to provide a positioning device for securing an intramedullary nail in a long bone.

The object according to the present invention is achieved with a positioning device having the features of claim 1.

In the following, the terms interlocking intramedullary nail and intramedullary nail are used synonymously.

The positioning device according to the present invention comprises a guide bow with an adjusting device. The adjusting device comprises at least a targeting device. The targeting device is designed to receive, in particular releasably, an interlocking device, e.g. an interlocking screw, or an instrument for acting on the interlocking device, e.g. a screwdriver, a drill or a spike wire (wire for the tension-fixing of the bone fragments or implants).

The guide bow comprises a sleeve guide, which in turn comprises a sleeve. The sleeve is arranged to be rotatable and/or displaceable relative to the sleeve guide. For this purpose, the sleeve guide comprises, e.g., a continuous longitudinal opening or a bone section (herein, both terms are used synonymously).

The sleeve comprises also a continuous longitudinal opening or a bone section, in or at which a guiding device may be, or is, arranged.

In all of the aforementioned or following embodiments, the use of the expression "may be" or "may have" and so on, is to be understood synonymously with "preferably is" or "preferably has" and so on, and is intended to illustrate and embodiment according to the present invention.

Whenever numerical words are mentioned herein, the person skilled in the art shall understand them as indications of numerical lower limits. Unless it leads the person skilled in the art to an evident contradiction, the person skilled in the art shall comprehend the specification for example of "one" encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Advantageous developments of the present invention are each subject-matter of the dependent claims and embodiments.

In some embodiments according to the present invention, the guiding device is preferably arranged in the sleeve to be displaceable and/or rotatable thereto.

In certain embodiments according to the present invention, the guide bow is arranged to be displaceable along the longitudinal axis of the sleeve relative thereto and to be rotatable about the longitudinal axis of the sleeve relative thereto.

In some embodiments according to the present invention, the guiding device comprises a connection section for releasable connecting the sleeve to the intramedullary nail.

In some embodiments according to the present invention, securing an intramedullary nail is to be understood as connecting the intramedullary nail to the interlocking screws. The intramedullary nail is secured in the bone by inserting the interlocking screws or devices. The positioning device according to the present invention therefore serves for fixation. It also serves for fixation or can be used for this purpose in some embodiments, respectively.

The guide bow having an adjusting device, which comprises a targeting device, may in some embodiments according to the present invention be referred to as a target bow. The target bow is preferably arched, at least in sections thereof.

In some embodiments according to the present invention, the interlocking device is an interlocking screw or an interlocking pin. However, the present invention is not limited thereto.

In some embodiments according to the present invention, the receiving device provided for receiving an interlocking screw in the intramedullary nail is a device with at least one prefabricated through opening for the interlocking screw. The receiving device may be sleeve-shaped or cylindrical. The receiving device may composed of several parts and/or several materials (composite). For example, a plastic ring may be used as part of the receiving device. The plastic ring may advantageously prevent an unintentional unscrewing of the interlocking screw In specific embodiments according to the present invention, the receiving device is an opening or a bore in the intramedullary nail.

In certain embodiments according to the present invention, the targeting device is prepared and/or designed for setting, positioning, guiding, aligning, drilling and/or screwing the interlocking device.

In some embodiments according to the present invention, the guiding device is to be understood as a hollow or tubular or preferably longitudinally extended device with a longitudinal through-opening. In some embodiments according to the present invention, the guiding device could also be referred to as a tensioning device or a receiving device for an intramedullary nail, e.g., for tensioning the intramedullary nail against the targeting device, e.g. against the sleeve.

In some embodiments according to the present invention, the guiding device is a tubular, internally-hollow rod or a hollow tube. The guiding device may be provided and prepared for the manual, releasable securing or fixing of the intramedullary nail at or in the sleeve.

In particular, the guiding device may have a handle, a knob or a similar arrangement at one axial end thereof for manually rotating the guiding device about its longitudinal axis, for example, when screwing the guiding device to the intramedullary nail. The handle or knob may, for example, be knurled.

The opposite end of the guiding device can carry a thread, preferably an external thread, or an external thread section.

The external thread may be matched to be connected to an internal thread or an internal thread section at an axial end of the intramedullary nail.

In specific embodiment according to the present invention, the guiding device for guiding a tool is provided and prepared for the force-fit locking of the receiving device and of the interlocking device guided in the receiving device. A force-fit locking can e.g., be achieved by screwing a threaded pin which acts in the intramedullary nail on the receiving device.

In some embodiments according to the present invention, the guiding device is designed to releasably interlock the intramedullary nail against the sleeve.

In specific embodiments according to the present invention, the guiding device is arranged coaxially with the longitudinal axis of the sleeve.

In some embodiments according to the present invention, the sleeve, in particular on an outer or peripheral surface thereof, comprises a sliding guide along which the guide bow or a section thereof may be moved along the sleeve or relative to the sleeve.

In some embodiments according to the present invention, the term "sliding guide", as used herein, describes a slot, web, recess or groove, each referred to as a slide, which is guided or force-guided into or on or along the one device, in particular the guide bow.

By means of the slide, the movement of the guide bow relative to the sleeve is predetermined or defined in some embodiments according to the present invention. The transfer function of the sliding guide determined and specified by the course of the slot, the web, the recess or the groove.

The sliding guide preferably serves, in particular, controlling or aligning the targeting device and the interlocking device received therein, in particular the interlocking screw, onto the prefabricated through-opening of the intramedullary nail for the interlocking screw.

The sliding guide can generate a combined displacement movement (in the direction of the longitudinal axis of the sleeve) and/or rotary movement (in the circumferential direction of the sleeve).

Furthermore, the sliding guide may specify an initial position and/or an end position of the displacement path.

The sliding guide may be a helical groove.

In certain embodiments according to the present invention, the slide is produced on the sleeve by means of erosion, cutting-shaping process, e.g. by milling or drilling or by laser processing of the sleeve.

In specific embodiments according to the present invention, the sleeve is produced together with the slide by means of an additive (generative) manufacturing method (e.g. by laser sintering).

In some embodiments according to the present invention, the slide is produced by means of an application method (e.g. welding).

In some embodiments according to the present invention, the sleeve comprises at least one snap-in position provided on or in the sleeve.

The snap-in position may serve to releasable secure or lock the guide bow in at least one predetermined position on the sleeve or relative thereto.

The snap-in position is preferably not integrated into the sliding guide, but is located separately from the latter, e.g., at least partially, on one side of the sleeve which faces the side with the sliding guide.

The snap-in position may be arranged, for example, in the circumferential direction of the sleeve, on an opposite side of the sleeve rotated by 180 degrees.

The snap-in position may be a recess in the lateral area of the sleeve. It may be a through-opening in the wall of the sleeve.

For example, the guide bow may be guided along the sliding guide on the one side of the sleeve (viewed in the circumferential direction of the sleeve) by means of a pin, which is integrated or inserted into the guide bow. On the opposite side of the sleeve, the guide bow may have a snap-in arrangement which is designed to engage or interact in the snap-in position, preferably to snap-in therein.

The snap-in position may be a form in the slide. It may be a through-hole or opening of the wall of the sleeve.

The snap-in position may be designed in order to allow the guide bow to be locked on the sleeve by means of clamping, snapping-in or form-fit.

The guide bow may be locked in one of the snap-in positions, for example, by means of a bolt or snap-in pin. Thus, its orientation to the sleeve is releasably fixed.

In some embodiments according to the present invention, the guide bow comprises at least one snap-in pin or bolt for releasably snapping-in the guide bow on or in the at least one snap-in position of the sleeve. An arrangement or positioning of the snap-in pin in a snap-in position may be referred to as a snap-in arrangement. If the snap-in pin is not snapped-in, one speaks of a non-snap-in arrangement. The snap-in pin may be arranged to be repeatedly moved between the two aforementioned positions, the snap-in arrangement and the non-snap-in arrangement.

In specific embodiments according to the present invention, the snap-in pin is arranged to be manually snapped-in or positioned and/or to be manually released or decoupled again. For such manual actuation, a transmission, a drive, a slide or slider or the like may be provided. The manual actuation may be spring-supported or assisted. Alternatively, the snap-in and/or the release or decoupling may be effected without manual actuation, e.g. by means of a spring-supported ball or a similar arrangement.

In some embodiments according to the present invention, the snap-in position has a longitudinal groove which is aligned in the circumferential direction of the sleeve, wherein a longitudinal groove may be a longitudinal groove, recess or through-opening in the lateral area of the sleeve extending in an arbitrary direction.

The longitudinal groove may allow a displacement of the snap-in pin or bolt, within the limits defined by the geometry, in the circumferential direction of the sleeve and relative thereto after the snapping-in of the snap-in pin into the snap-in position. The permitted displacement of the snap-in pin after the snapping-in may be referred to as a play of the snap-in pin in the snap-in position. The play may be predetermined by the shape of the longitudinal groove, in particular by its length. For example, such play may allow the interlocking screw to be aligned, displaced or positioned within a through-opening for the interlocking device (e.g. a long hole or a bore) in the intramedullary nail within predetermined (one-side or multiple-side) limits.

In certain embodiments according to the present invention, the longitudinal groove is designed to move or rotate/pivot the interlocking device or interlocking screw with a play in a defined dimension or circumference, e.g. +/−10° in the circumferential direction of the sleeve, e.g. with respect to the center of the through-opening in the intramedullary nail.

In some embodiments according to the present invention, the guide bow comprises a locking device, in particular a fixing screw, for preferably manually locking, by means of the snap-in pin, the guide bow in a selected, predetermined snap-in position of the guide bow relative to the sleeve.

After the locking, the guide bow cannot be moved relative to the sleeve anymore.

In certain embodiments according to the present invention, the sleeve comprises markings by means of which the current position of the guide bow relative to the sleeve can be controlled or monitored.

The snap-in position or the sliding arrangement on or in the sleeve may be concealed when the guide bow is moved in the sliding guide such that a user of the positioning device according to the present invention does not see the current or instantaneous position of the guide bow between the snap-in positions or in the slide. However, it may be helpful for the user, for example to recognize in which of the several snap-in positions the snap-in pin of the guide bow is currently located or situated. This may advantageously facilitate and simplify the further positioning of interlocking screws in the intramedullary nail by the positioning device according to the present invention. Therefore, the sleeve may have an orientation aid for the user, which reproduces or reflects the slide or the sliding guide in a visible region for the user on the surface of the sleeve. In such embodiments according to the present invention, the slide may be impressed or visualized on the sleeve in this visible region, e.g. by engraving in mirror image.

In specific embodiments according to the present invention, the guiding device, for releasably connecting the sleeve to the intramedullary nail, is arranged inside the sleeve and preferably coaxially or parallel to the longitudinal axis of the sleeve.

In order to be able to use the positioning device according to the present invention for securing the intramedullary nail, it is intended to connect the positioning device to the intramedullary nail to be fixed. The connecting arrangement provided for this purpose comprises a first and a second component.

The first component may be a web-groove connection for the twist-proof of the opposite arrangement of sleeve and intramedullary nail. For example, the sleeve comprises, at an axial end, at least one, but preferably two, three or more (for example axial) webs, protrusions, pins or steps which engage in a corresponding number of (for example axial) grooves, slots or recesses at an axial end of the intramedullary nail. Alternatively, the intramedullary nail may have the steps or the like and the sleeve may have the grooves or the like. Combinations thereof are possible.

After the sleeve and the intramedullary nail are arranged to each other so as to be twist-poof and preferably also in a predetermined manner, the sleeve and the intramedullary nail can be releasably connected. This second component may be realized by means of the guiding device. For this, the guiding device may be arranged inside the sleeve and coaxially with the longitudinal axis of the sleeve. The guiding device may be inserted through the sleeve and screwed together with an internal thread or internal thread section of the intramedullary nail by means of an external thread or external thread section arranged at the axial end of the guiding device. The guiding device thus releasably braces the intramedullary nail against the sleeve and hence holds it in the guide bow, preferably in a predetermined orientation with respect to the latter.

By means of the two components described above, it may advantageously be achieved that the intramedullary nail does not rotate or turn or twist in the direction of the screw rotation while it is being screwed to the guiding device or while the screwing is released, for example after securing the intramedullary nail by the interlocking screw(s). Avoiding a turning or a rotation, even though only slightly, e.g. in the range of only few degrees, may be advantageous and important for the later stability of the long bone.

In some embodiments according to the present invention, the guiding device is tubular or hollow inside and thus designed for guiding or guiding through a tool. The tool may, e.g., be used of actuating or screwing (tightening and releasing) a locking or blocking device in the interior of the intramedullary nail. The locking or blocking device may be designed as a clamping screw for securing or clamping an adjustable receiving device for an interlocking screw.

For example, the tool for screwing or clamping may comprise an internal thread pin in the intramedullary nail. The tool may be an Allen key. The tool may, for example, be configured to apply a torque of, e.g., approximately 5 Nm or 9 Nm or range between 5 to 9 Nm.

In certain embodiments according to the present invention, the adjusting device is displaceable, in a limited or unlimited manner, along the guide bow together with the targeting device, which is to be aligned on the intramedullary nail. The displacement direction along the guide bow is defined as the x-direction. The targeting device is designed to receive an interlocking device, in particular an interlocking screw, or an instrument for acting on the interlocking device. Thus, with the aid of the positioning device according to the present invention, the interlocking device may be aligned and positioned, in a superimposed movement, on the sleeve along the guide bow in the x-direction and corresponding to the position of the guide bow relative to the intramedullary nail corresponding to the sliding guide, in order to subsequently secure the interlocking screw in the intramedullary nail.

In some embodiments according to the present invention, the guide bow is designed, at least in section, as a circular bow or in a circular bow shape. The adjusting device is thereby, at least in section, displaceable along a circular bow.

In specific embodiments according to the present invention, the targeting device comprises one or more openings which face the intramedullary nail and reach through the adjusting device. The opening(s) is/are designed in particular for receiving an interlocking device or an instrument for acting on the interlocking device disposed in a receiving device of the intramedullary nail.

In specific embodiments according to the present invention, the guide bow comprises stops for limiting the displacement path of the adjusting device along the guide bow. Die The stops may advantageously improve the handling of the positioning device according to the present invention, e.g., in that the adjusting device may be aligned faster or easier with a desired, selected or targeted through-opening in the intramedullary nail. The stops may also be provided with regard to an anatomically more senseful positioning of the interlocking device.

In some embodiments according to the present invention, the targeting device is displaceably arranged in the circumferential direction of the sleeve in the longitudinal direction of the guide bow (x-direction) and perpendicular to the longitudinal direction of the guide bow (y-direction. Through this displaceability in both the x-direction and the y-direction, an instrument, which may be connected to a locking device, may be moved and positioned in the targeting device within a circular section. The circular surface of this circular section may be stretched by the x-direction and the y-direction. The targeting device may be arranged perpendicular to this circular surface. The center of the circle lies in particular in the receiving device for the interlocking screw in the intramedullary nail, here in particular at the intersection of the receiving device of the interlocking screw and longitudinal axis of the intramedullary nail (or the longitudinal axis of the sleeve). The intramedullary nail and the positioning device may be correspondingly match to each other. The movement of the instrument on the circular surface and it positioning may be compared with the movement and operation of a joystick.

In certain embodiments according to the present invention, the targeting device arranged to be displaceable in the adjusting device and relative thereto or to the guide bow.

In some embodiments according to the present invention, the adjusting device is arranged to be movable in at least a first position, here referred to as the adjustment position, for moving the targeting device relative to the adjusting device or the guide bow. In at least a second position, here referred to as a fixed position, the adjusting device for securing the targeting device is not movable relative to the adjusting device or to the guide bow, which may in particular be effected by means of frictional connection.

The securing of the targeting device relative to the adjusting device or relative to the guide bow is preferably releasable.

The first position is provided, in particular, for positioning and aligning the interlocking screw with the desired receiving device in the intramedullary nail. After the alignment is completed and the interlocking screw should subsequently be secured in the receiving device or through the latter in the long bone, the targeting device is secured relative to the adjusting device (second position). In this position, the targeting device can no longer be displaced or moved relative to the guide bow. Then, by means of an instrument which is connected to an interlocking screw and which is arranged in the targeting device, the interlocking screw can advantageously be simply and securely fixed in the desired position in the The positioning and/or securing of the targeting device relative to the adjusting device may take place in different ways. The various embodiments are based, in particular, on a 3-shell model or a 3-shell arrangement. The radial outer shell may be a section of the guide bow. The radial outer shell may be the adjustment device or a section thereof. In the middle shell between the inner shell and the outer shell, in particular the targeting device is integrated. The middle shell is movable and/or positionable between the outer and the inner shells. The securing of the middle shell, after the positioning and alignment of the targeting device has been completed, may be carried out in different ways. Exemplary examples of this securing are described below.

A first concept for securing the middle shell is referred to herein as a spring pin concept. One or more spring pins, which are integrated, for example, into the outer shell press with their spring force directly or indirectly onto the middle shell. By means of these pressing forces, the middle shell is pressed onto or against the inner shell and secured in a contact therewith by means of frictional force. The contact pressure forces can be varied on the basis of the number and/the spring strength of the spring pins so that, on the one hand, the targeting device remains movable, on the other hand, the frictional forces are high enough to allow exact locking of the interlocking screw when the positioning and alignment are completed.

A second concept is referred to here as a flap concept. The outer shell is hinged on one side. A device for fixing or clamping the outer shell with the inner shell is arranged on a position (on the upper side of the shell) opposite to the hinged outer shell. For example, the outer shell may be secured and clamped on or against the middle and inner shell by means of a wing screw, an eccentric, a snap hook or the like. When this device secures the outer shell to the inner shell, for example by manually tightening a wing screw, the middle shell in which the targeting device is arranged is clamped and immovable. If, on the other hand, this device is released, the middle shell may be moved and thus the targeting device may be positioned and aligned.

A third concept is referred to here as a spring concept. The middle shell comprises two shells radially arranged above each other. The two shells arranged above each other are radially pushed apart by springs arranged between these two shells. Furthermore, at least one of the two shells may comprise surface structures, for example protrusions, which may engage in further surface structures on the radial inner side of the outer shell on the opposite side. The surface structure on the inner side of the outer shell may, for example, be bores into which the protrusions engage or snap-in.

A fourth concept is referred to as a thread concept. The middle shell comprises two separately-produced shells, being arranged radially above each other, which are connected to each other by a thread. Due to the rotation of one of the two shells relative to the second shell, the shells are, depending on the direction of rotation, either turned together or turned apart, i.e., their spacing is reduced or increased. If these two shells are turned apart, the inner and outer shells are spun and thus fixed.

A fifth concept uses a lever action to clamp the outer shell against the middle shell or to release a tension. In the basic state, the outer shell presses, in the spun state, against the middle shell, which in this basic state is fixed or immovable. When the outer shell is pressed radially outwards by or is bent outward by a lever effect, the middle shell loosens. The targeting device may be aligned and positioned until the outer shell is returned to the basic state and the middle shell is secured. The lever effect is applied, in particular using manual force.

Some or all of the embodiments according to the present invention may have one, several or all of the advantages mentioned supra and/or in the following.

By means of the positioning device according to the present invention, it is advantageously possible to correct, during an operation, minor misalignments when positioning and/or when screwing of interlocking screws into an intramedullary nail arranged in the long bone.

The position and the angle of bores for the interlocking screws and their position may advantageously be adapted still intraoperatively to the individual anatomical situation and to an injury-caused situation by means of the positioning device according to the present invention.

Furthermore, by means of the positioning device according to the present invention, the angle of the interlocking screw penetrating or reaching through the intramedullary nail may still be varied intraoperatively in order, e.g., to reposition the fracture fragments or to correctly adapt them anatomically.

By means of the snap-in arrangement of the positioning device according to the present invention, the snap-in arrangement may advantageously be locked in a defined position along the longitudinal axis of the sleeve by a form-fit between the bolt of the snap-in arrangement of the guide bow and the sleeve. Furthermore, this form-fit or positive connection may be implemented or executed, by means of a long hole, in the circumferential direction of the sleeve in order to provide or allow a defined or limiting rotation between the guide bow and the sleeve. This enables the surgeon within certain limits to intraoperatively align the interlocking devices relative to the intramedullary nail.

By means of the markings for the position control of the guide bow relative to the sleeve, the surgeon may advantageously be aided to trace or monitor the position of the snap-in position and/or of longitudinal holes along the longitudinal axis of the sleeve. By means of markings, the position of the snap-in positions and/or long holes or longitudinal grooves may be advantageously visualized. The orientation (rotation direction and indication of the angle of the guide bow relative to the sleeve) of the guide bow relative to the intramedullary nail or of the through-openings for screwing the locking screws into the intramedullary nail may thus be advantageously facilitated.

By the present invention, the positioning device may be securely and simply connected, releasably, to the intramedullary nail to be secured. Thus, the positioning device may be decoupled and removed from the secured intramedullary nail. In this, the first component, a web-groove connection, may serve the torsion-proof mutual arrangement of the sleeve and the intramedullary nail. It may advantageously ensure that the intramedullary nail is not rotating or turning during the screwing of during the release of the screw connection between the guiding device and the intramedullary nail. This contributes to not jeopardizing the position of the intramedullary nail in the bone, through applying of torque, when connecting the positioning device to the intramedullary nail or when releasing or decoupling the positioning device from the intramedullary nail.

The present invention is exemplarily explained with regard to the accompanying figures, in which identical reference numeral refer to the same or similar elements. The following applies in the schematically simplified figures, respectively:

FIG. 19 shows a two-piece targeting device of the positioning device;

FIG. 20 shows an adjusting device having a snap-in device for securing the targeting device at the guide bow;

FIG. 21 shows the targeting device having a hole arrangement for an instrument;

Figure 22:
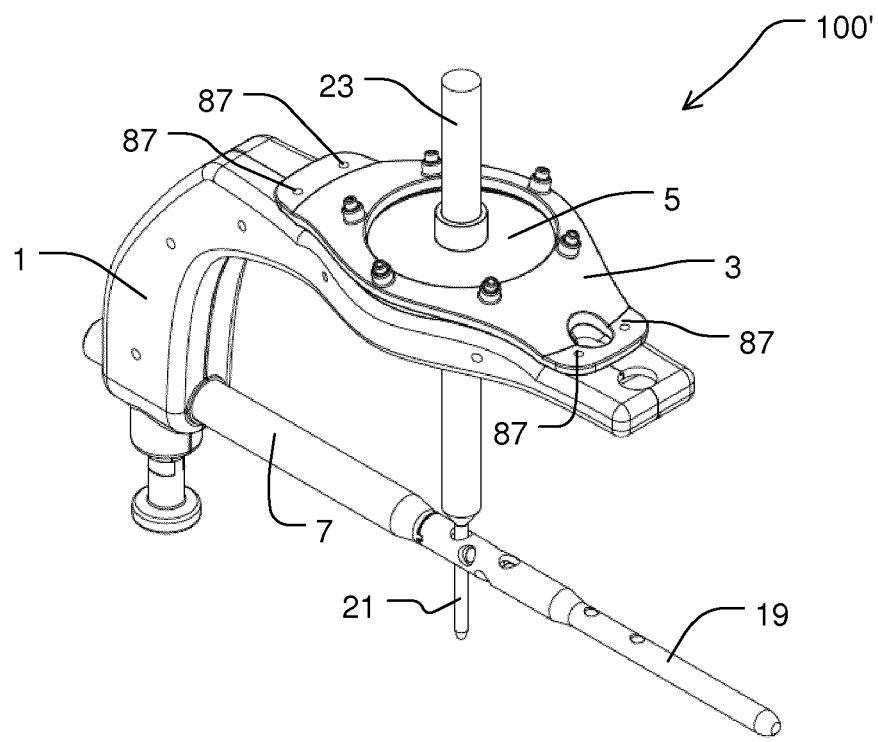
FIG. 22 shows the positioning device of FIG. 10 in a further view.
Figure 23:
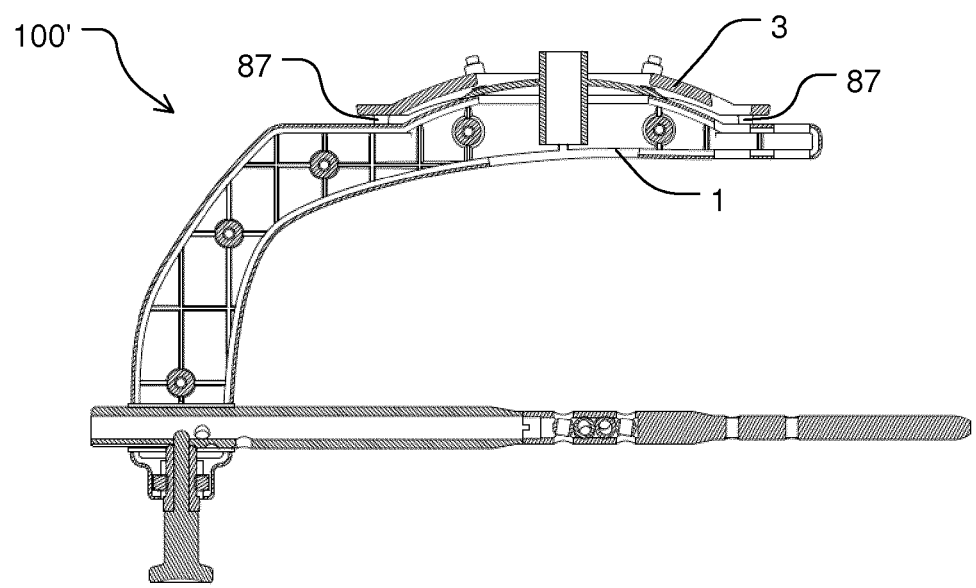
Figure 24:
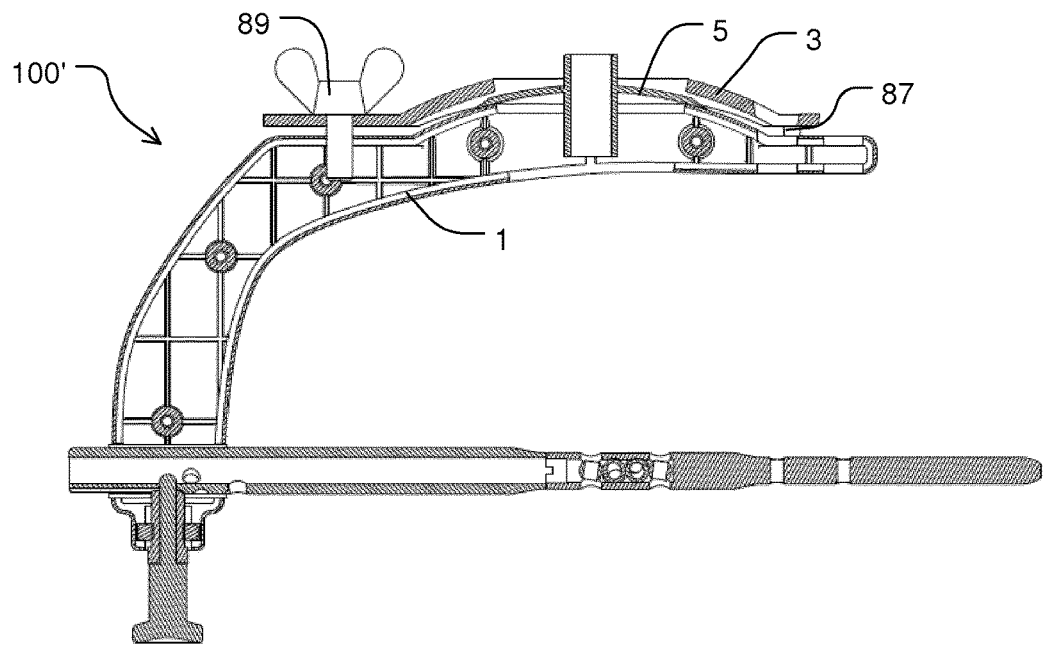
Figure 25:
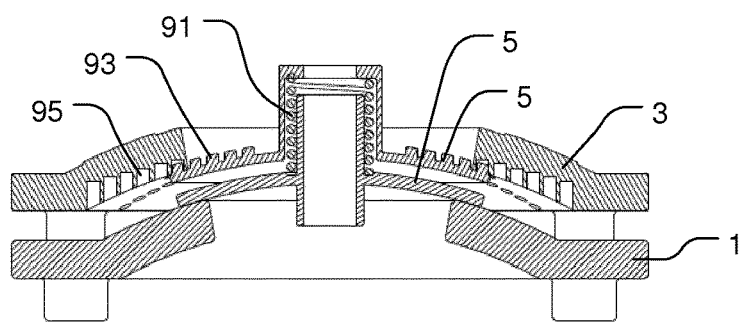
Figure 26:
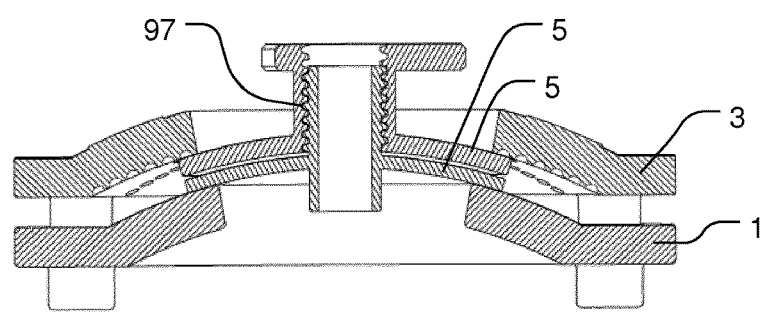
Figure 27:
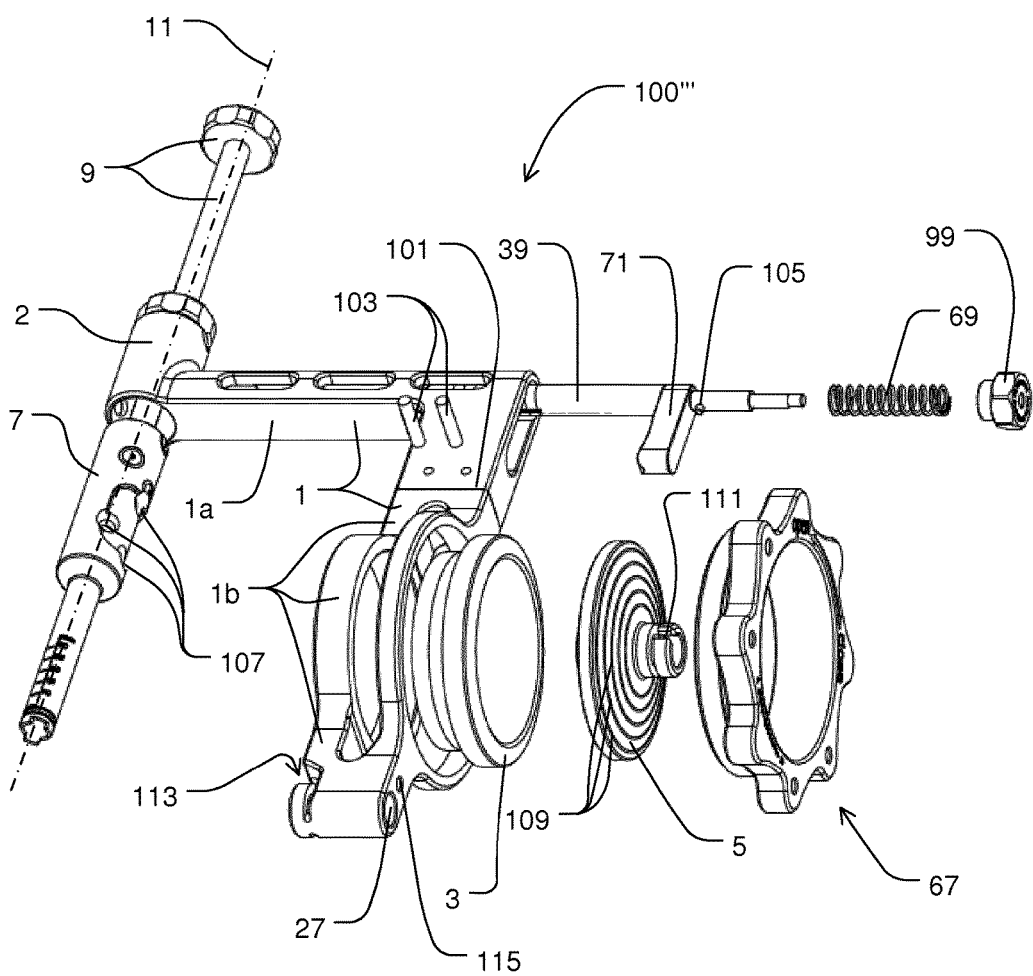
Figure 28:
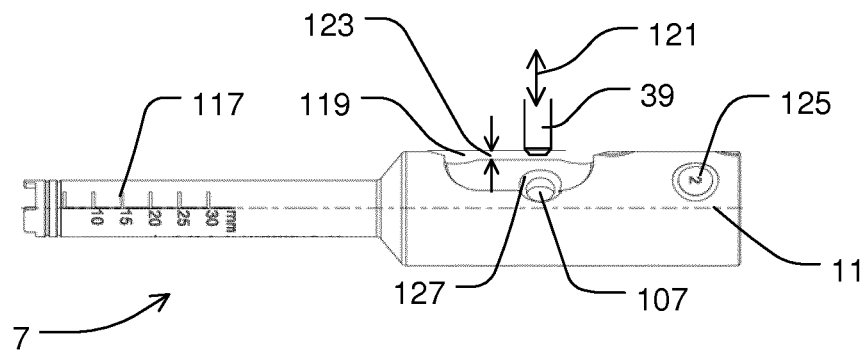
Figure 29:
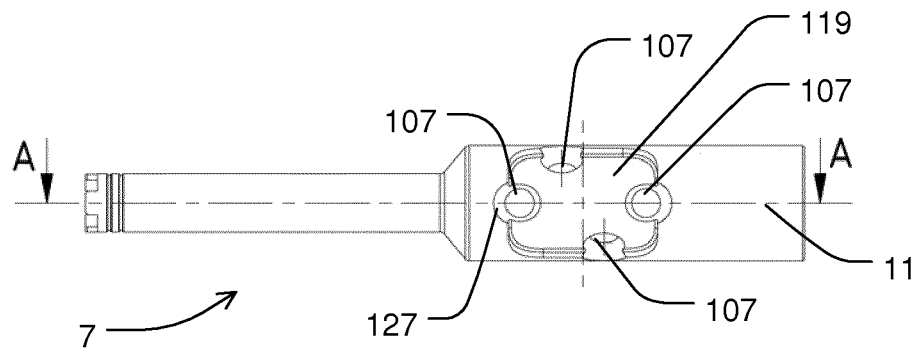
Figure 30:
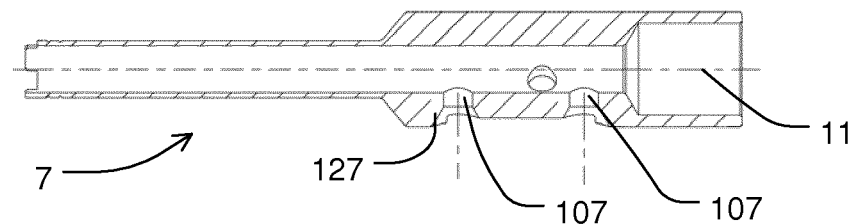
Figure 31:
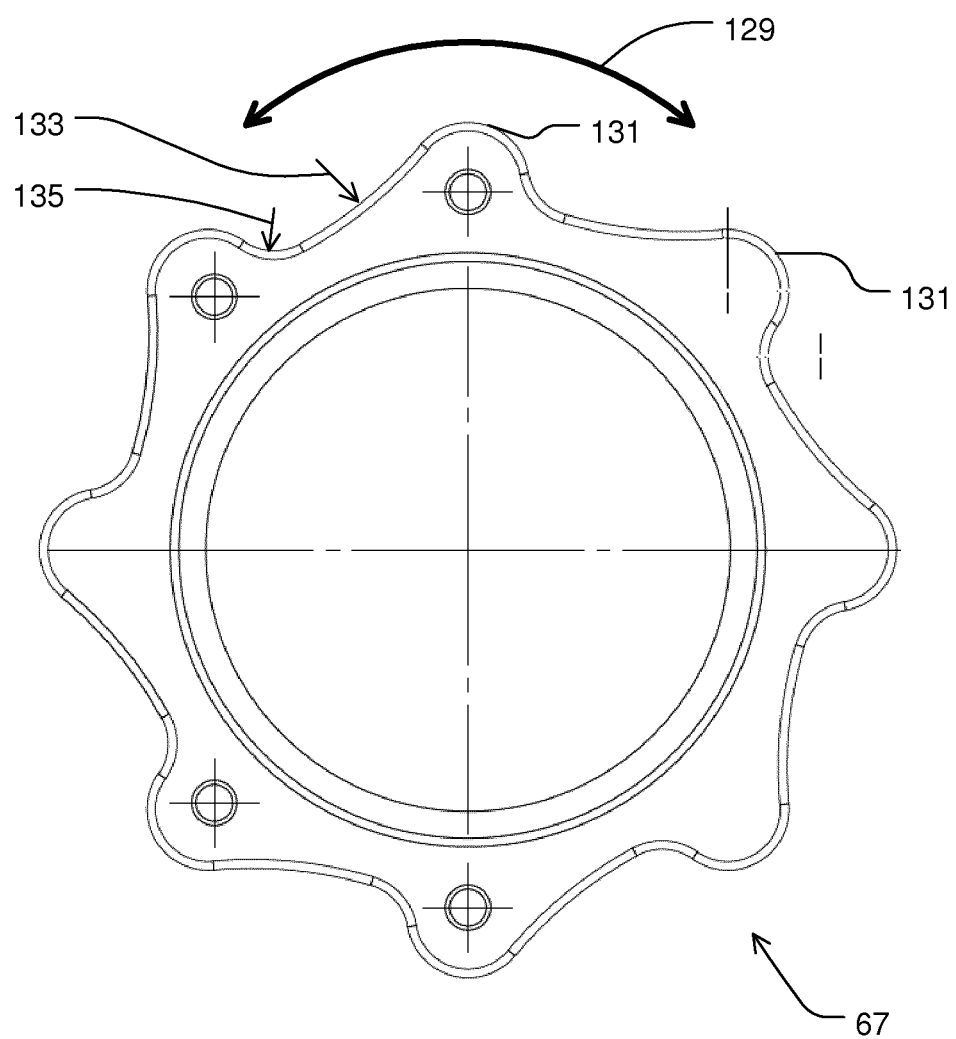

FIG. 23 g; shows a sectional view of the positioning device of FIG. 22;

FIG. 24 shows a sectional view of the positioning device of FIG. 22 with a flap concept for securing the adjusting device on the guide bow;

FIG. 25 shows the targeting device, which is movably arranged between the adjusting device and the guide bow by means of a spring concept;

FIG. 26 shows a targeting device, which is movably arranged between the adjusting device and the guide bow by means of a thread concept;

FIG. 27 shows a further embodiment of the positioning device according to the present invention;

FIGS. 28 to 30 show different views of a further sleeve without a sliding guide; and FIG. 31 shows a further rotary tightener.

Figure 1:
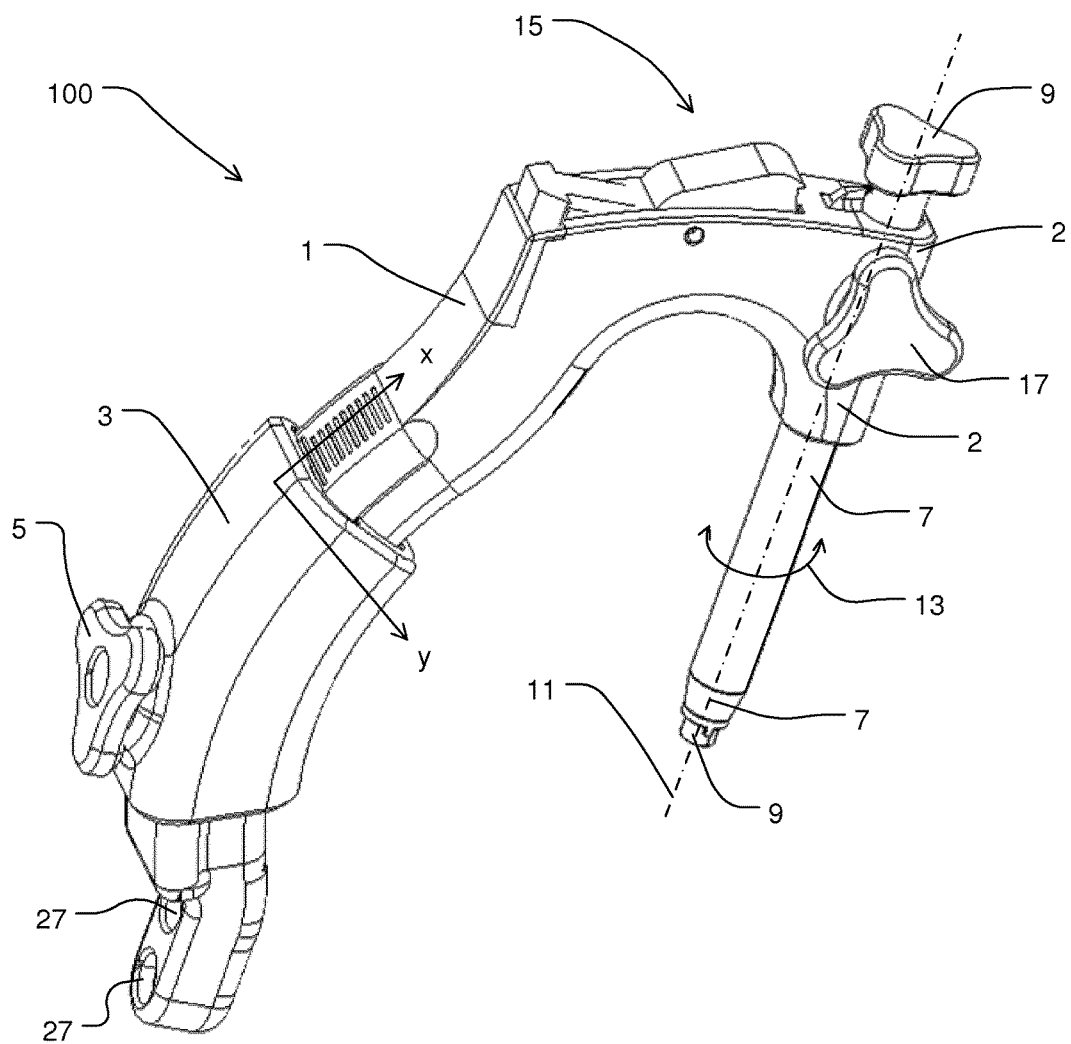
FIG. 1 shows a perspective view of a first exemplary embodiment of a positioning device according to the present invention.

FIG. 1 shows a perspective view of a first exemplary embodiment of a positioning device 100, obliquely from the top. The positioning device 100 comprises a guide bow 1 with a sleeve guide 2, an adjusting device 3 and a targeting device 5, a sleeve 7 and a guiding device 9.

The guide bow 1 receives the sleeve 7 in the sleeve guide 2 and can be slid or moved relative to the sleeve 7 about a longitudinal axis 11 of the sleeve 7 and/or can be rotated about the longitudinal axis 11 in the circumferential direction 13 of the sleeve 7. The sleeve 7 preferably comprises a sliding guide 29 (or a predetermined pathway) for the sliding or rotating of the guide bow 1 (see FIG. 5). Along the sliding guide 29, there are optional positions (see FIG. 5), at which the guide bow 1 may preferably be snapped-in by means of a snap-in arrangement 15.

If, like in the example of FIG. 1, a snap-in arrangement 15 is provided then it is possible in certain embodiment according to the present invention, after a complete snap-in, to manually fix the guide bow 1 on or at the sleeve 7 by means of a locking screw 17 or by other fixation means; or the guide bow 1 may be prevented from rotating further and/or from moving or sliding in a longitudinal direction relative to the sleeve 7. After having been fixed, the guide bow 1 is positioned in the final position in order to secure an intramedullary nail by an interlocking screw (see FIG. 2).

If such fixation is provided, then it is done for example through frictional connection or form-fit or positive connection between the locking screw 17 and the sleeve 7.

The optionally provided adjusting device 3 is movable in x-direction along the guide bow 1. After the final position of the adjusting device 3 has been reached through moving, then the adjusting device 3 may be secured or fixed on the guide bow 1 by means of the targeting device 5, which, in this embodiment, is exemplarily a locking screw at the same time, or by means of another fixation device and/or it may be clamped by means of a frictional connection. For this purpose, the targeting device 5 preferably comprises a form which is easily grasped, e.g. the triangular form shown in FIG. 1, so that it can be manually fixed.

The guiding device 9 has an opening (not shown in FIG. 1) at its upper end (referring to FIG. 1). It also has a further opening at its lower end, so that it offers or forms a continuous cavity for receiving a tool 55 (not shown in FIG. 1, see FIG. 13), for locking or interlocking the intramedullary nail 19 (also not shown in FIG. 1) or for receiving other objects. The longitudinal axis of the guiding device 9 runs preferably parallel to the sleeve 7, in which the guiding device 9 is received, or becomes identical to the longitudinal axis 11 of the sleeve 7.

In addition, the positioning aids 27 may be provided for positioning the interlocking screws on the positioning device 100.

Figure 2:
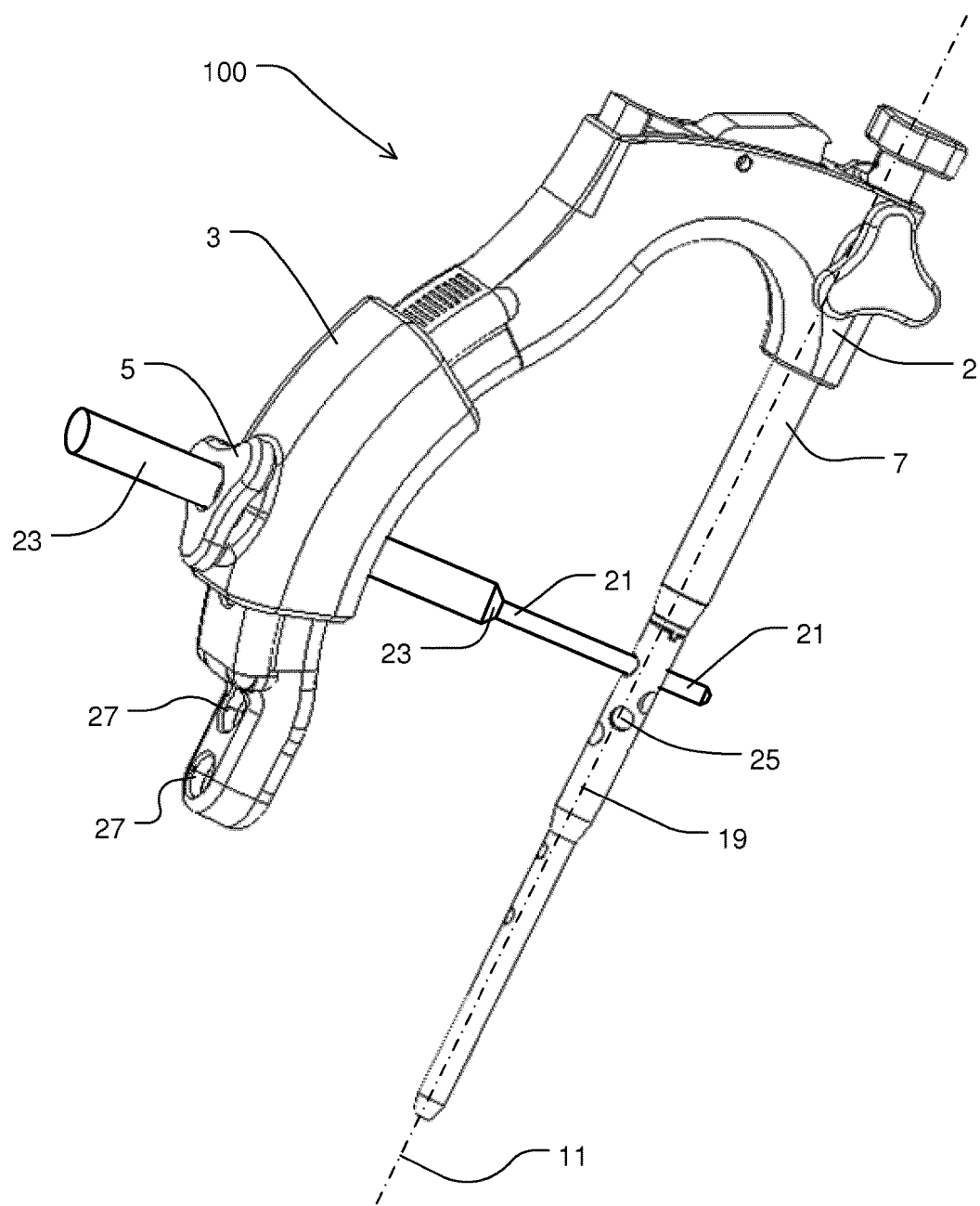
FIG. 2 shows the positioning device of FIG. 1 according to the present invention having an intramedullary nail, an interlocking screw and an instrument for inserting the interlocking screw.

FIG. 2 shows the positioning device 100 of FIG. 1 according to the present invention with an intramedullary nail 19, an interlocking screw 21 and an instrument 23 for inserting the interlocking screw 21. The instrument 23 is guided through the targeting device 5 and in the present example also through at least one section of the guide bow 1.

Prior to inserting or screwing the interlocking screw 21 into the intramedullary nail 19, the guide bow 1 may, as already described in FIG. 1, be move along the longitudinal axis 11 and/or may be rotated about the latter in the circumferential direction of the sleeve 7. Furthermore, the adjusting device 3 may be moved along the guide bow 1 in x-direction. This positioning (moving and rotating) is continued until an alignment on a targeted opening or a through-opening 25 in the intramedullary nail 19 is achieved and the interlocking screw 21 can be fixed in the intramedullary nail 19 and in a long bone surrounding the intramedullary nail 19 (not shown in FIG. 2). The positioning device 100 according to the present invention advantageously makes it possible to continue with this positioning of the interlocking screw 21 (and if appropriate further interlocking screw 21) after inserting the intramedullary nail 19 into the long bone, and thereby aiming at or heading for or steering to different through-openings 25 by the targeting device 5, until, in the view of the user, an optimum positioning of one or more interlocking screws 21 has been reached.

In addition, further interlocking screws 21' may in turn be screwed through the positioning aids 27, or by means thereof, into the intramedullary nail 19. These positioning aids 27 do not offer any possibilities for positioning along the longitudinal axis of the guide bow 1 and thus do not offer a fixed, predetermined, possibly also vertical (relative to the longitudinal axis 11) or angled positioning of the interlocking screws 21 into the intramedullary nail 19. These positioning aids 27 may be referred to as so-called immobile or fixed target bores or rather distal interlocking screws 21'.

Figure 3:
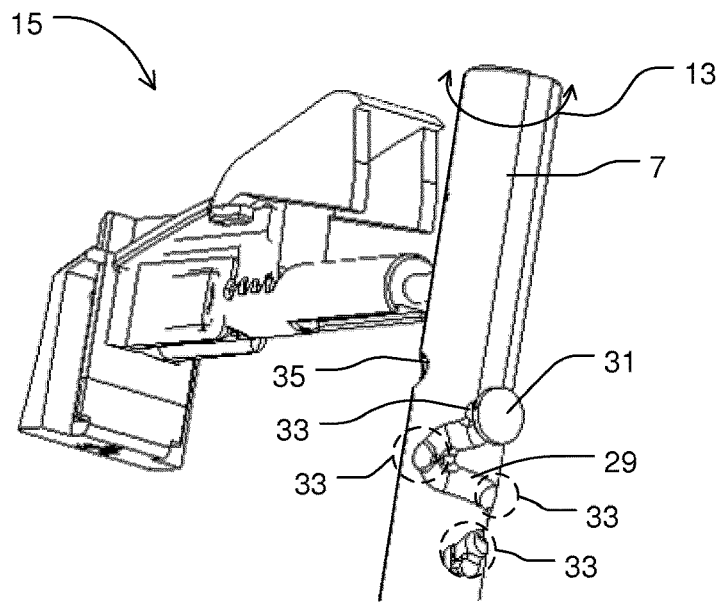
FIG. 3 shows a section of the positioning device according to the present invention having a sleeve and a sliding guide in the sleeve, as well as a snap-in arrangement.

FIG. 3 shows an inner section of the positioning device 100 with a sleeve 7 and a sliding guide 29 in or on the sleeve 7, and the snap-in arrangement 15. A cover covering the components in FIG. 3 during use of the positioning device 100, which cover is part of the guide bow 1, is not illustrated in FIG. 3, however in FIG. 4, for the sake of clarity.

A guide step 31 (or pin), which is illustrated as a single part in FIG. 3 in a simplified manner, however is integrated into the guide bowl and is part of the sleeve 7, allows through its engagement in the sliding guide 29 of the sleeve 7 a form-fit or a positive connection between the guide bow 1 or the sleeve guide 2 and the sleeve 7. The guide bow 1 is guided into or along the sliding guide 29 by means of the guide step 31.

Alternatively, the guide step 31 may be integrated into the sleeve 7 or connected thereto. In this case the sliding guide 29 is integrated into the sleeve guide 2 (see FIG. 4).

The sliding guide 29 is straight in an upper part thereof (referring to the illustration of FIG. 3, i.e. between the upper end of the sleeve 7 and the guide step 31). By means of this straight sliding section, the guide bow 1 is introduced into the sleeve 7 during the assembly of the positioning device 100 according or the present invention (or vice versa).

Alternatively, the guide bow 1 may also be connected or mounted on the sleeve 7 differently. For example, the outer diameter of the sleeve 7 in the upper area (above the sliding guide 29) could be smaller by twice the depth of the straight groove of the sleeve 7 than the outer diameter shown in FIG. 3 so that the guide step 31 can slide over the entire circumference at the upper end of the sleeve 7

The sliding guide 29 may be designated as helical groove in a lower part thereof. In the lower area, the sliding guide 29 is not, or substantially not, straight, but rather wound, twisted, looped or the like.

The guide bow 1 is therefore guided or at least limited in a predefined path by means of the sliding guide 29 during its use. The guide bow 1 may thus be moved only along the path indicated by the sliding guide 29 or limited therefrom relative to the sleeve 7 and/or may be slid and/or turned and/or rotated only in predetermined positions.

Guiding the guide step 31 into the sliding guide 29 may also be referred to as a form-fit or positive spring-groove connection.

Extensions 33 are provided in the example of FIG. 3 at the curved or bent points along the sliding guide 29, and as part of the latter. Its longitudinal axis preferably extends substantially or exclusively in the circumferential direction 13 of the sleeve 7, respectively. These extensions 33 mark or code for so-called snap-in positions 35 on the side of the sleeve 7 opposite of the circumferential direction 13, into which a bolt or snap-in pin 39, described below, may be snapped-in or engaged. Snap-in positions 35 may be designated as longitudinal holes in the circumferential direction 13. The snap-in positions 35 and their function are described in more detail in FIG. 5. The structure and the function of the snap-in arrangement 15 are also described in more detail in FIG. 5.

Figure 4:
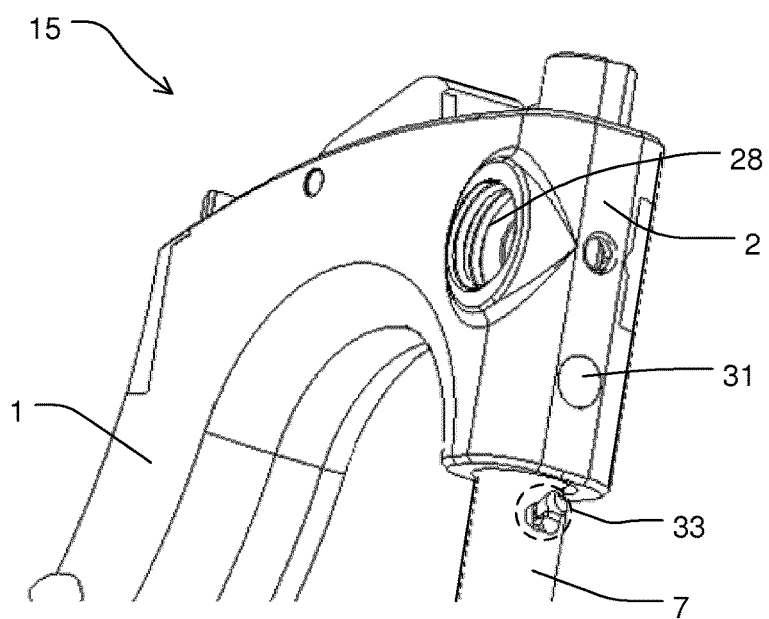
FIG. 4 shows the section of the positioning device of FIG. 3 according to the present invention.

FIG. 4 shows the section of the positioning device of FIG. 3 according to the present invention being inserted into the upper section of the guide bow 1. In this view, the guide step 31 is integrally arranged in the guide bow 1. The sleeve 7 is received into the receiving section of the guide bow 1 for the sleeve, the sleeve guide 2. The sliding guide 29 is concealed by this; only the lowest, groove-shaped extension 33 is recognizable or seen.

Furthermore, FIG. 4 shows an inner thread 28 with a conical step for receiving the locking screw 17 (see FIG. 1).

Figure 5:
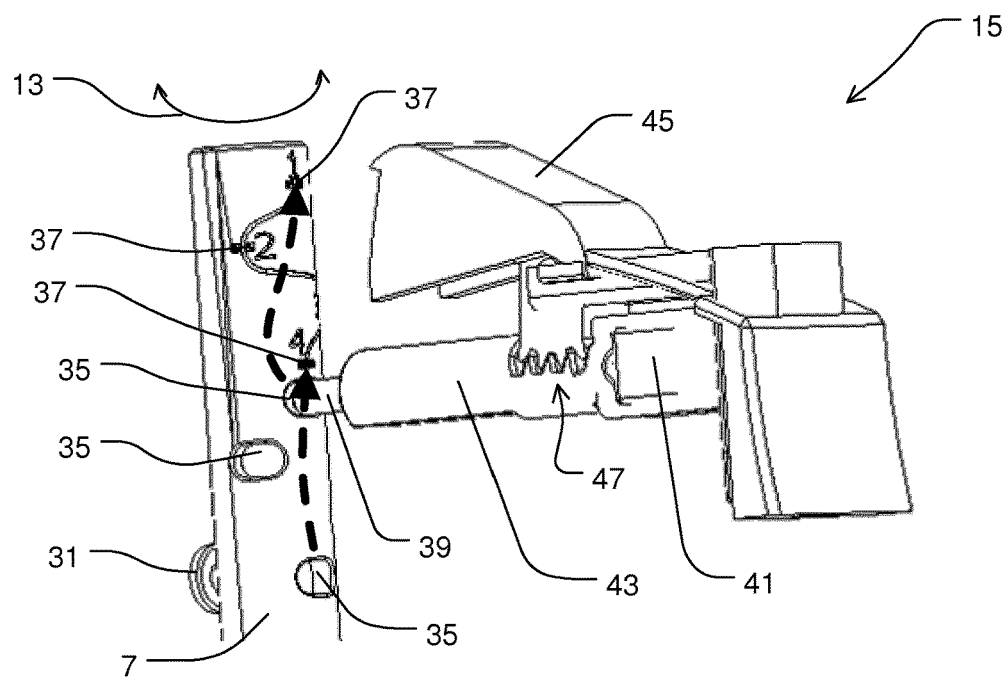
FIG. 5 shows the section of the positioning device of FIG. 3 according to the present invention having several snap-in positions and markings for position control.

FIG. 5 shows the section of the positioning device 100 of FIG. 3 according to the present invention in a further view. A plurality of snap-in positions 35 as well as markings for position control 37 can be seen. The view in FIG. 5 is rotated about 180 degrees in circumferential direction 13 relative to view of FIG. 3 and FIG. 4.

The snap-in positions 35 with the groove-shaped extension 33, the sliding guide 29 (see FIG. 3) and the markings correspond to the position control 37 ("1", "2" and "4", the position "3" is concealed and not visible). For example, the marking "1" corresponds to the uppermost snap-in position which is, in FIG. 5, snapped-in with the bolt 39. This arrangement corresponds to the arrangement in FIG. 3 and FIG. 4, in which the guide step 31 is illustrated in the upper most groove-shaped extension 33 of the sliding guide 29.

A locking of the snap-in arrangement 15, and thus of the guide bow 1, into which the snap-in arrangement 15 is integrated and which is fixed by means of the locking with respect to the sleeve 7 or is restricted in further movement or rotation relative to the sleeve 7, occurs by means of a form-fit or positive connection between the bolt 39 and the snap-in position 35 at a predetermined and predefined position of the sleeve 7. Prior to snapping-in the bolt 39 in a snap-in position 35, the bolt 39 may act on the sleeve 7 by means of a preload, in particular one achieved by a spring. The bolt 39 is then guided (frictionally) along the sleeve 7.

The snap-in position 35 is designed as a long hole but may also have other arbitrary shapes. In a long-hole shape of the snap-in position 35, the guide bow 1 may move within the long hole in circumferential direction 13 of the sleeve 7. This so-called play of the guide bow 1 in the sleeve 7 may facilitate the positioning and screwing of the interlocking screw 21 in the intramedullary nail 19. (See FIG. 2).

The markings for the position control 37 ("1", "2", and "4") are visualization aids and thus orientation aids for the user of the positioning device 100 with respect to the direction of the rotation and/or the information of an angle of the guide bow 1. The user may easily determine or trace the state of the snap-in positions 35 with the aid of these markings 37.

The locking of the bolt 39 in one of the snap-in positions 35 occurs by means of a snap-in arrangement. In the snapped-in state, in which the bolt 39 is inserted in the snap-in position 35, a tensioning device, e.g. a double leaf spring 41, such as that of FIG. 5, pushes on the bolt arrangement 43 (corresponds to an extension of the bolt 39) and positions or interlocks it into the snap-in position 35. An undesired slipping out of the bolt 39 out of the snap-in position 35 may thereby be advantageously prevented. Decoupling of the snap-in position 35 is effected by, in particular manually, pressing down the lever 45 (or by actuating another suitable device) which pulls out or decouples the bolt arrangement 43 and thus the bolt 39 by means of, e.g., gear connection 47. Following the decoupling, the guide bow 1 can be again moved, relative to the sleeve 7, along the path of the sliding guide and may for example be positioned in a further snap-in position 35.

Figure 6:
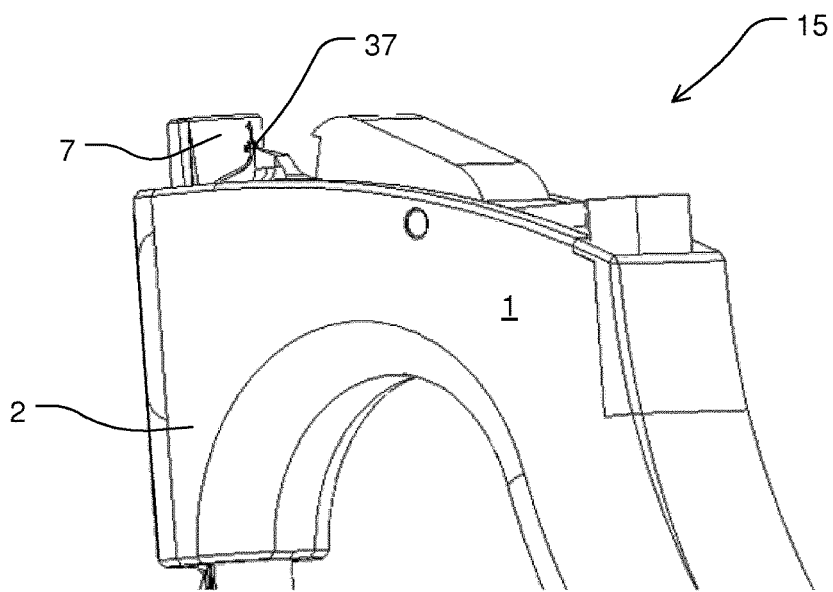
FIG. 6 shows the components of the positioning device of FIG. 5 according to the present invention with a guide bow.

FIG. 6 shows the components of the positioning device 100 according to the present invention which are seen in FIG. 5 concealed at least by a section of the guide bow 1, which, as explained already in FIG. 4, conceals the snap-in arrangement 15.

In the present example, the guide bow 1 conceals all four snap-in positions 35 such that the user is initially unable to recognize in which snap-in position 35 the bolt 39 is snapped-in. For this reason, the marking 37 for position control is optionally provided on the upper surface of the sleeve 7. It is seen in FIG. 6 that the bolt 39 is in the upper snap-in position 35, since the marking 37 shows or indicates "1", i.e. the upper marking 37, compare to FIG. 5.

Figure 7:
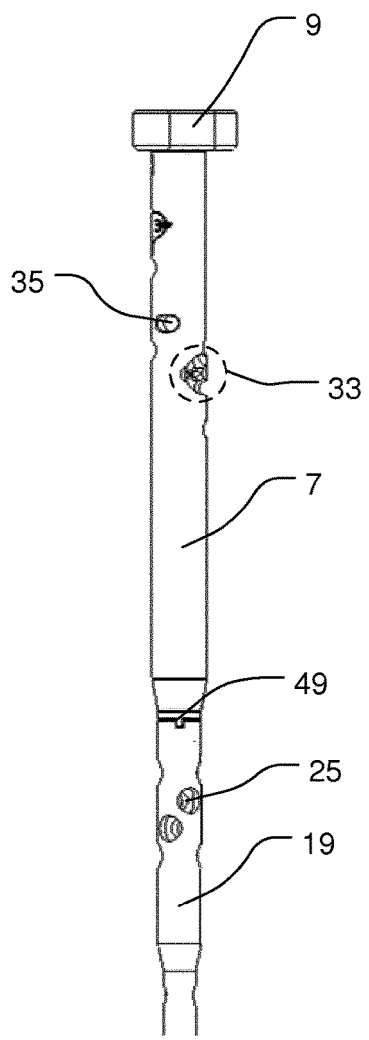
FIG. 7 shows a guiding device having a sleeve connected to an intramedullary nail.

FIG. 7 shows the guiding device 9 inserted into a sleeve 7, comprising a long hole and connected to the intramedullary nail 19.

The sleeve 7 is connected, by way of example, to the intramedullary nail 19 by means of two bars 49 (only the front bar 49 is visible in FIG. 7), wherein the bar 49 is inserted into the grooves of the intramedullary nail 19 in a form-fit or positive connection. This connection may be referred to as spring-groove connection. For securing the sleeve 7 to the intramedullary nail 19, an optional thread 51 (external thread) is screwed into an inner thread of the intramedullary nail 19, if present, at the lower end of the guide device 9. The intramedullary nail 19 is thus fixed (adapted) on the sleeve 7 in such a way that it cannot rotate nor slide. The position of the sleeve 7 relative to the intramedullary nail 19 is thus preferably fixed both in longitudinal and circumferential direction.

Figure 8:
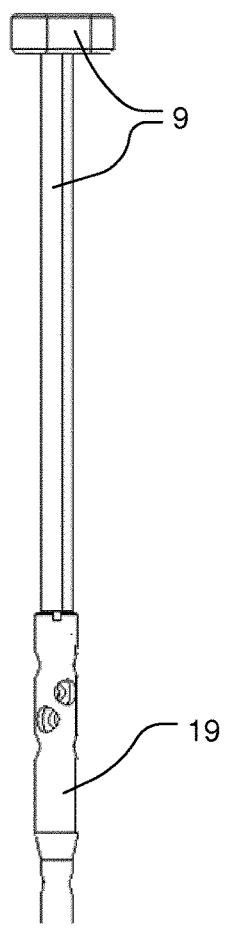
FIG. 8 shows the guiding device of FIG. 7 having the intramedullary nail, but without the sleeve.

FIG. 8 shows the guiding device 9 of FIG. 7 with only the intramedullary nail 19, without sleeve 7.

Figure 9:
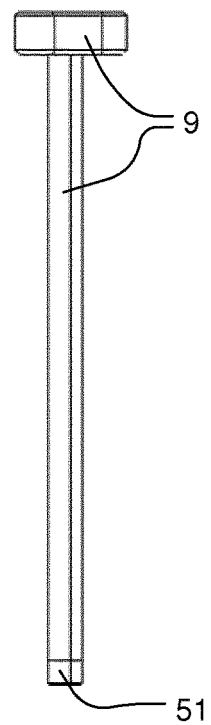
FIG. 9 shows the guiding device of FIG. 7.

FIG. 9 shows the guiding device 9 of FIG. 7 as a single part with the outer thread 51 at the lower end of the guiding device 9.

Figure 10:
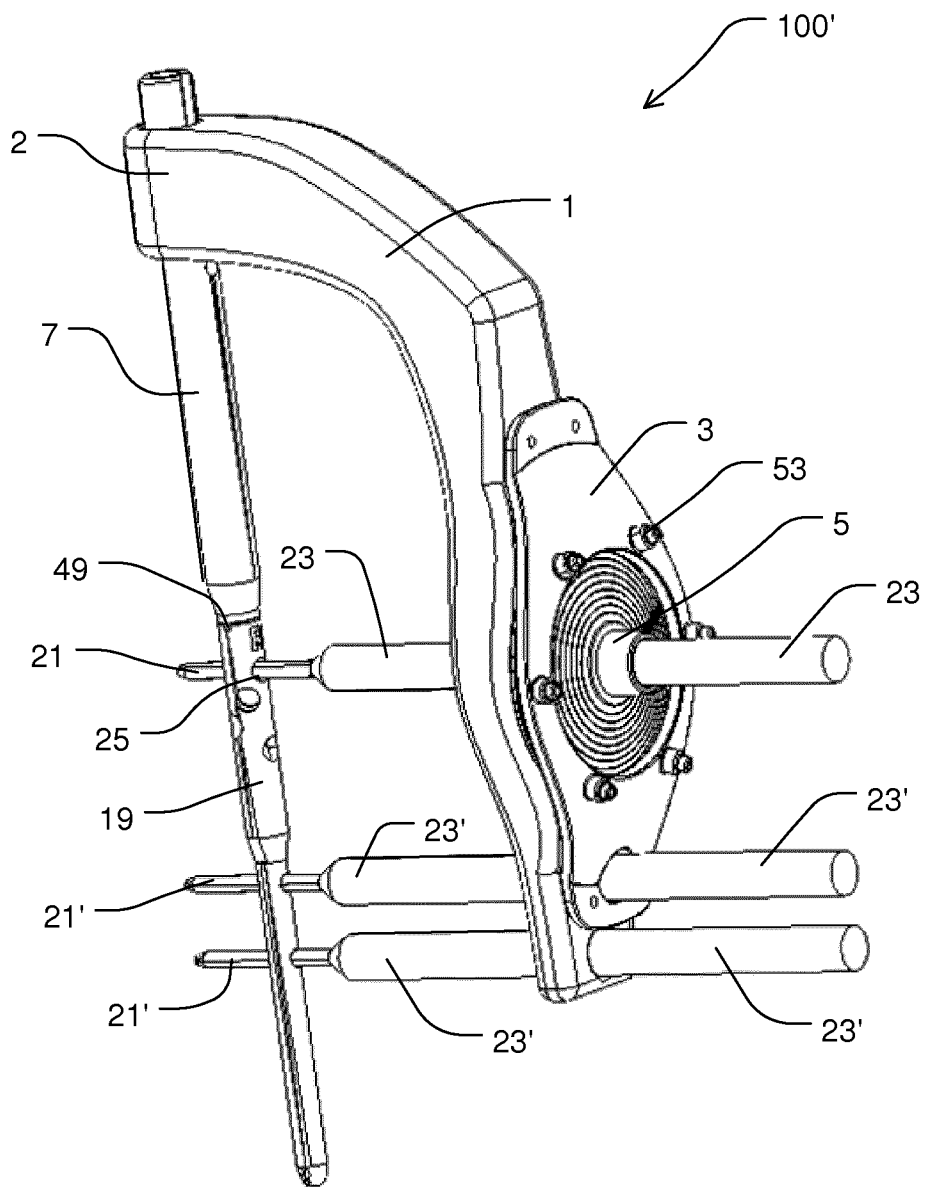
FIG. 10 shows a further embodiment of the positioning device according to the present invention, wherein the targeting device is arranged between the adjusting device and the guide bow by means of a spring pin concept.

FIG. 10 shows a further embodiment of a positioning device 100 according to the present invention.

The adjusting device 3 is designed as a section of a spherical surface with a circular opening. The form or shape of the adjusting device 3 may likewise have a differently designed upper surface instead of a spherical surface, only optionally curved or straight.

The adjusting device 3 is secured on the guide bow 1 (the more detailed description of this securing is explained in FIGS. 22 and 23).

The exemplary circular opening in a central or middle area of the adjusting device 3 is provided for guiding the targeting device 5 and the instrument 23 (which serves inserting the interlocking screw 21). The longitudinal axis of the instrument 23 is perpendicular to the spherical surface. The extension of the longitudinal axis of the instrument 23 extends through the center of the bore or through-opening in the intramedullary nail 19.

The instrument 23 is guided into the targeting device 5. The targeting device 5 is optionally shell-like formed with annularly concentrically arranged grooves, notch or protrusions about the middle guide of the instrument 23. The shell-like formed targeting device 5 may be referred to as a middle shell, which, viewed in the radial direction, is arranged between the outer shell which corresponds to the adjustment device 3 and the inner shell which corresponds to the shell-like surface of the guide bow 1.

The targeting device 5, i.e. the middle shell, may be moved or slid between the interior and the exterior. In this movement, optional pins 53, supported in radial direction by a spring, engage in the annular grooves or notches of the targeting device 5. A defined and exact positioning of the instrument 23, and thus of the interlocking screw 21, is thus possible. The distances between the grooves correspond to a specific and predetermined deflection of the targeting device 5, which may be indicated at an angle or degree number. In this embodiment, the deflection between two annular grooves corresponds to an angle or a degree number of (1°) degree. This principle or concept with pins 53 supported by a spring, which pins engage into the groove, may be referred to as a spring-pin concept.

The arrangement of the pins 53, radially supported by a spring, on the radial outer surface of the targeting device 5 is shown in FIG. 2, in which the adjusting device 3 (outer shell) has been removed for better clarity.

Figure 11:
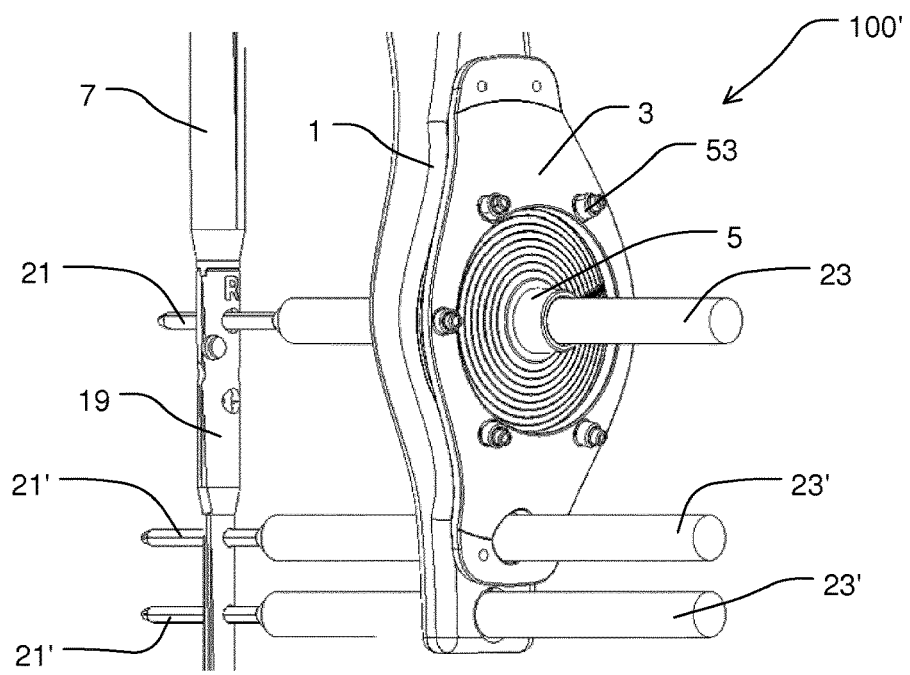
FIG. 11 shows a detail view of an adjusting device having a targeting device of the positioning device of FIG. 10.
Figure 12:
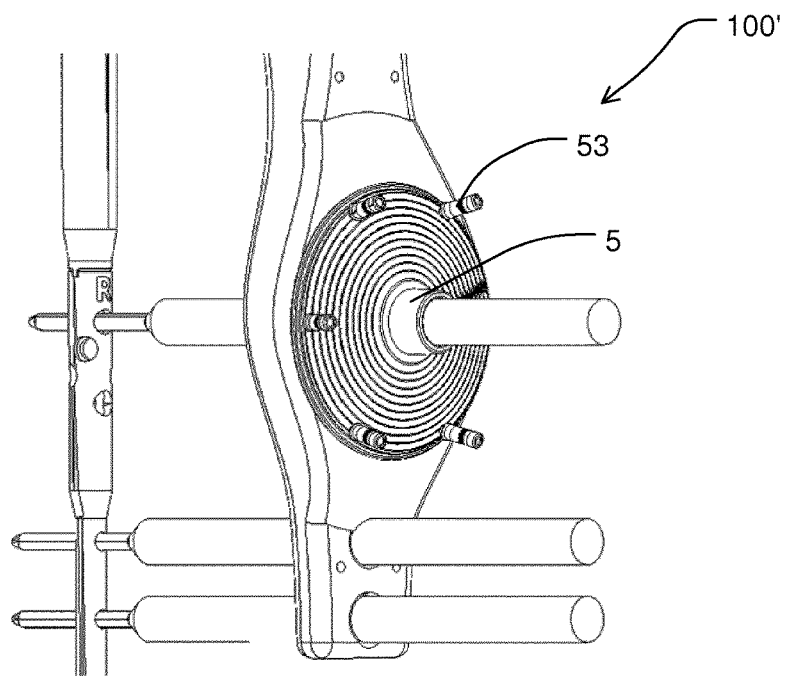
FIG. 12 shows the detail view of FIG. 11 without an outer shell of the adjusting device.

The arrangement in FIG. 10 allows the instrument 23 (and thus the interlocking screw 21) to deflect from the desired or predetermined degree (or degree range), for example of ten degrees (10°) compared to the centrical initial position in the middle (this initial position is shown in FIGS. 10, 11 and 12 and is referred to as a zero-degree position (0°)).

By means of an optional combined form-fit or positive connection (between the pins 53 and the annular groove of the targeting device 5) and a frictional connection (between the middle and the outer shell), securing the position of the instrument 23 for screwing in or fixing the interlocking screw 21 is, hence, rendered possible.

The targeting device 5 may optionally rest on a circular section of a structure which is arranged under the targeting device 5. In this way, it may be ensured that the targeting device 5 is preferably guided at a constant distance from a target point.

FIG. 11 shows a detailed view of FIG. 10 with the adjusting device 3 (outer shell), the targeting device 5 (middle shell), the guide bow 1 (inner shell), the sleeve 7, the intramedullary nail 19 and the instrument 23 for inserting the interlocking screw 21. Furthermore, non-movable instruments 23' (the targeting device 3 is not movable relative to the guide bowl) for interlocking or screwing of further interlocking screws 21' are illustrated.

FIG. 12 shows the view from FIG. 11 without the adjusting device 3 (outer shell) for illustrating the position of the pins 53 on the targeting device 5 (middle shell).

Figure 13:
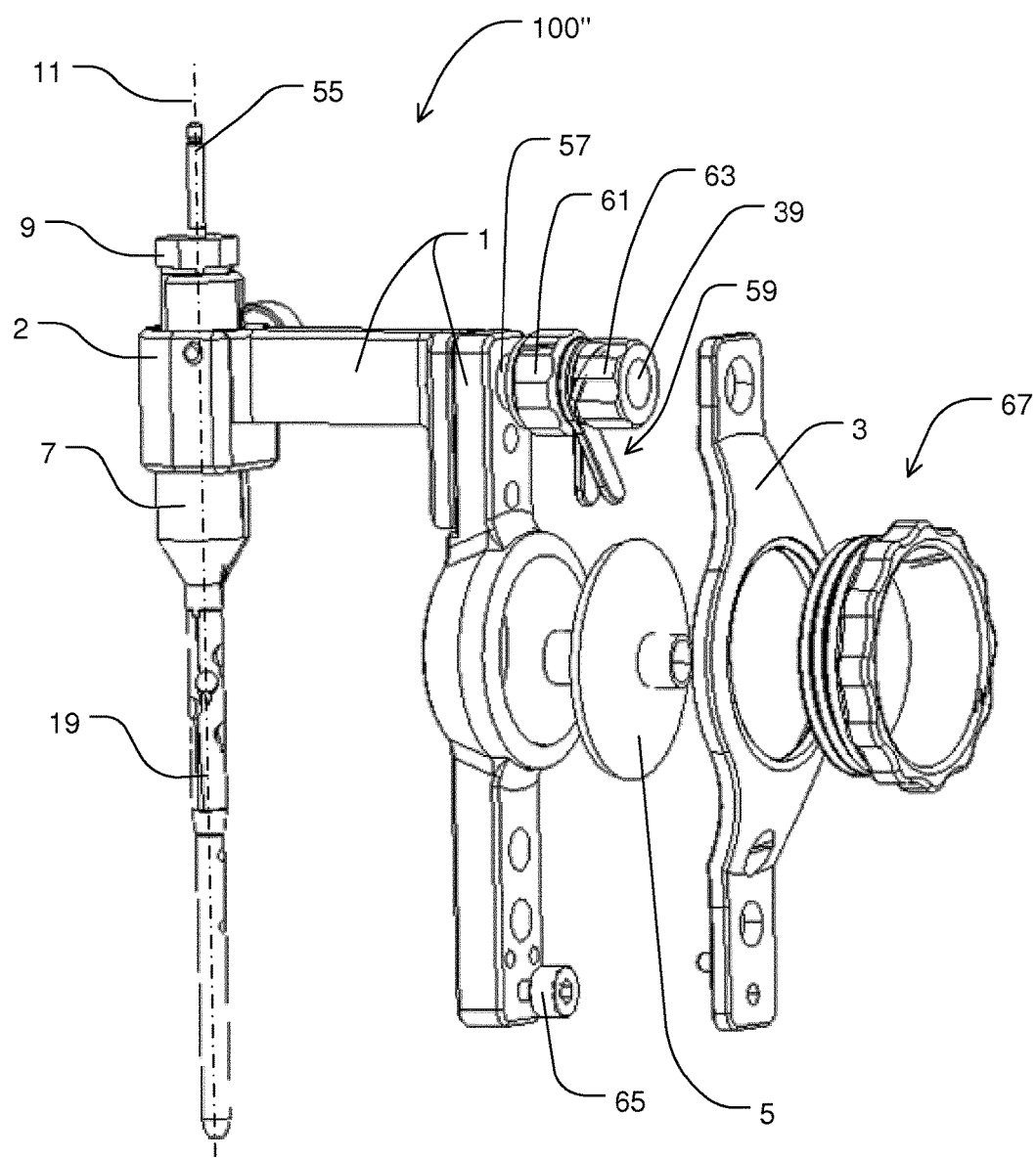
FIG. 13 shows a further embodiment of the positioning device according to the present invention.

FIG. 13 shows a further embodiment of the positioning device 100" according to the present invention.

The guide bow 1 is halved in this embodiment. A first section (in FIG. 13, the left section) of the halved guide bow 1 comprises the sleeve guide 2, is exemplarily straight and extends substantially perpendicular to the longitudinal axis 11 of the sleeve 7. The guiding device 9 is introduced into the sleeve 7, in which guiding device 9 the tool 55, for example a hexagonal turner, is guided along the longitudinal axis 11, e.g., for locking the intramedullary nail 19. Alternatively, other objects instead of the tool 55 may also be guided by the guiding device 9.

The first section is connected to a second section (in FIG. 13, the right section) of the guide bow 1. The second section comprises the targeting device 5. The connection of the two sections may be achieved, e.g., by means of a connector 57. The snap-in pin 39 (or bolt of the snap-in arrangement), which is concealed in FIG. 13 by the guide bow 1 and is explained in detail in FIG. 4 as a further snap-in arrangement 15', is guided into the connector 57. The snap-in pin 39 is preferably actuated or moved by at least one lever 59 or a differently designed arrangement. The function of the lever 59 is described in more detail in FIG. 14.

Figure 14:
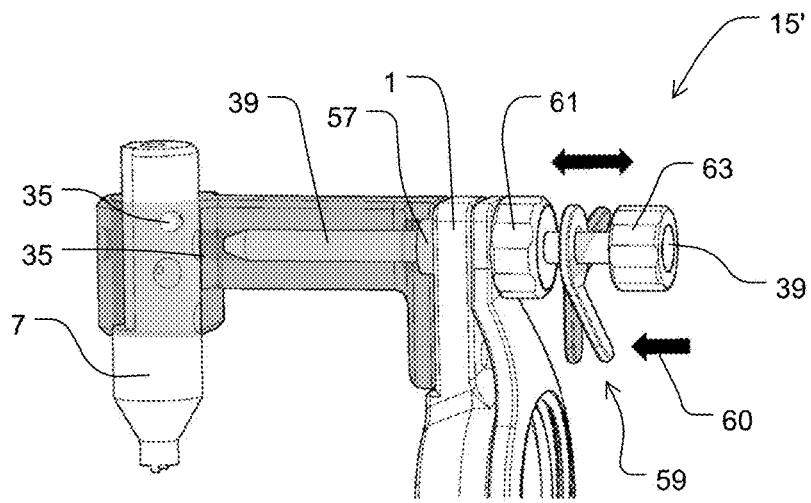
FIG. 14 shows the snap-in arrangement of the embodiment of FIG. 13 in detail.

The second section of the guide bow 1 comprises the adjusting device 3 as well as the targeting device 5, which are shown in FIG. 13 in exploded view, i.e., in the non-assembled state. In the assembled state, the adjusting device 3 is connected, e.g., to the connector 57 at the upper end (referring to the view in FIG. 13), as shown in FIG. 14.

The adjusting device 3 is connected to or fixed to, e.g. at the lower end thereof, the second section of the guide bow 1 by means of a connecting screw 65.

The targeting device 5 is secured between the adjusting device 3 and the second section of the guide bow 1 by a so-called rotary tightener 67.

Regarding the function of the targeting device 5, reference is made to the description of FIG. 10.

FIG. 14 shows the further snap-in arrangement 15' of the embodiment of FIG. 13.

The snap-in arrangement 15' is based on a magnetically supported fixing of the snap-in pin 39 into the snap-in position 35. The magnetic coupling is realized by a magnet or magnetic material, or presently by two magnets 61, 63 which may be arranged at the outer end of the snap-in pin 39 and which, facing each other, have different polarities. The first magnet 61 may be connected, e.g., to the connector 57 and/or to the guide bow 1. The second magnet 63 may be connected to the outer end of the snap-in pin 39. By means of the lever 59, the two magnets may be pushed apart and thus uncoupling or pulling out the snap-in pin 39. For this purpose, the lever 59 is pressed inwards in the direction of the arrow 60, so that the snap-in pin 39 and the magnet 63 are pushed outwards due to the angled or tilted lever 59.

Figure 15:
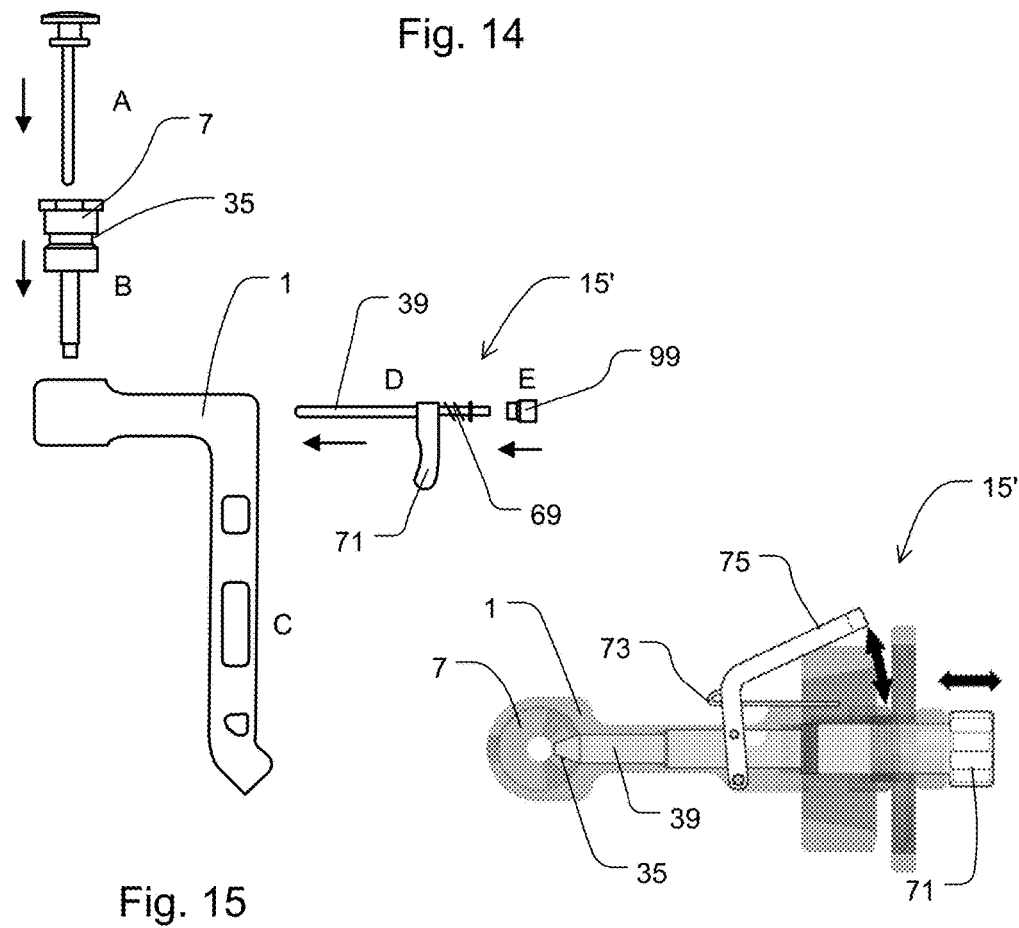
FIG. 15 shows a further snap-in arrangement having a spiral spring.

FIG. 15 shows a further snap-in arrangement 15' with the snap-in pin 39, a handpiece 71, a spiral spring 69 and a screw 99. For assembling, the parts A and B are first introduced into the guide bow 1 in the direction of the arrow. Then the parts D and E (snap-in pin 39, handpiece 71, spiral spring 69) are introduced into the guide bow 1 in the direction of the arrow. Subsequently, the screw 99 (part E) is screwed into the guide bow 1, thus securing the snap-in pin 39, the handpiece 71 and the spiral spring 69 in the guide bow 1. During this assembly step, the handpiece 71 has been pushed through the guide bow 1, which is hollow inside, in the angular range. It then protrudes out of the guide bow 1 in the angular range. In this snapped-in state, the spiral spring 69 is compressed and pre-stressed. For decoupling the snapped-in pin 39 out of the snap-in position 35 in the sleeve 7, the snap-in pin 39 is pulled outward by manually pressing the handpiece 71 in the guide bow 1, the snap-pin 39 is pulled out of the snap-in position 35 and the spiral spring 69 is further compressed. After a renewed positioning of the guide bow 1, the snap-in pin 39 can be snapped-in back into one of the snap-in positions 35 of the sleeve 7 by returning the handpiece 71 inward and by relaxing the spiral spring 69 back to its initial state.

Figure 16:
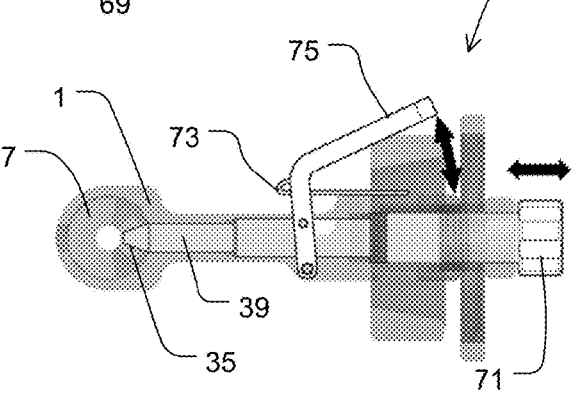
FIG. 16 shows a further snap-in arrangement having a leaf spring

FIG. 16 shows a further snap-in arrangement 15' with a leaf spring 73 and a lever 75. As shown in FIG. 15, the leaf spring 73 is tensioned by pressing down the lever 75 and/or due to tensioning. Concurrently with the tensioning of the leaf spring 73, the snap-in pin 39 is pulled out of the snap-in position 35 and decoupled therefrom by means of the handpiece 71. After a new positioning of the guide bow 1, the snap-in pin 39 can again be brought into a further snap-in position 35 in the sleeve 7 and locked therein.

Figure 17:
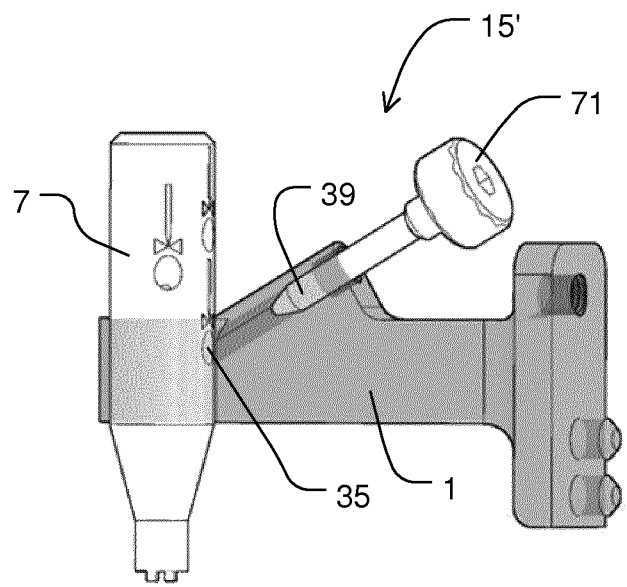
FIG. 17 shows a further snap-in arrangement having a snap-in pin for inserting the latter into the sleeve obliquely from above.

FIG. 17 shows a further snap-in arrangement 15' with a snap-in pin 39 (the snap-in pin 39 may be referred to as a plug-in bolt) which is inserted into a snap-in position 35 in the sleeve 7 obliquely from the top.

Figure 18:
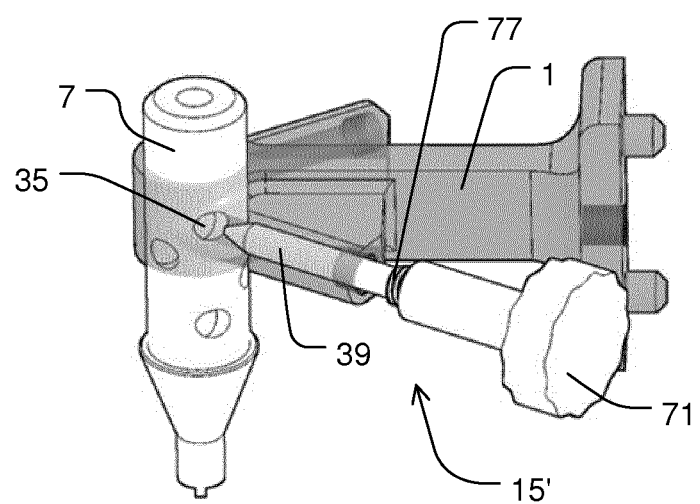
FIG. 18 shows a further snap-in arrangement having a snap-in pin for inserting it into the sleeve from the side.

FIG. 18 shows a further snap-in arrangement 15 with a snap-in pin 39 for laterally inserting the latter into a snap-in position 35 of the sleeve 7. The snap-in pin 39 may be secured after having been snapped-in by actuating or rotating the handpiece 71 and an optional thread 77.

FIG. 19 shows a halved targeting device 5 of the embodiment in FIG. 13. Two sections of the targeting device 5 may, e.g., be screwed together by a thread 79. The outer thread of the left section, in FIG. 15, of the halved targeting device 5 is screwed into the inner thread of the right section, in FIG. 15, of the targeting device 5.

Various advantages may be obtained by a halved targeting device 5. For example, a combination of different materials (higher stiffness of a connector for guiding an instrument for inserting the interlocking device or the interlocking screws 23, 23'; see e.g. FIG. 2) or an increase of the stiffness of the targeting device 5.

FIG. 20 shows a side view of an adjusting device 3 with a snap-in device 81 for securing the adjusting device 3 on the guide bow 1. The direction of the arrow shows the direction for closing, locking or snapping-in the adjusting device 3 on or at the guide bow 1. The snap-in device 81 is in particular elastically deformed or bent during the snap-in process, so that the snap-in device 81 is hooked at the guide bow 1 after having been snapped-in. For decoupling, the snap-in device 81 may be elastically or bent up and opened.

In the decoupled state, the targeting device 5 may, e.g., be replaced or adapted.

FIG. 21 shows a further targeting device 5 with a hole arrangement 83 for an instrument 23 (see FIG. 22). Compared to the embodiments of the targeting device 5, e.g. in FIG. 11 or FIG. 12, in which the targeting device 5 comprises only one hole, wherein the targeting device 5 is movable three-dimensionally in a plurality of directions between the guide bow 1 and the adjusting device 3, the targeting device 5 in FIG. 21 is rotatable only about an axis (the middle axis of the of the cylindrical targeting device 5). This limitation of movement may be advantageous, for example, in order to limit the angles for an instrument 23 in the respective holes and thus to limit the angles for placing the interlocking screws 21 by the positioning device 100.

The targeting device 5 may be secured by a locking screw 85.

FIG. 22 shows a further view of the positioning device 100' of FIG. 10 with the guide bow 1, the adjusting device 3, the sleeve 7, the intramedullary nail 19, the targeting device 5 as well as the instrument 23 for inserting the interlocking screw 21. The annularly arranged grooves shown in FIG. 10 are not shown in the simplified illustration of FIG. 22.

The adjustment device 3 is connected to the guide bow 1 by means of (for example) four (optional) point-shaped fixation.

FIG. 23 shows the positioning device 100' of FIG. 22 in a sectional view.

FIG. 24 shows the positioning device 100' of FIG. 22 in a sectional view with a flap concept for securing the adjusting device 3 on the guide bow 1. In this exemplary embodiment, the flap concept comprises only two (or optionally only one) point-shaped fixation 87 on one side of the adjusting device 3. The fixation 87 may for example be designed as a joint. On the opposite side, the adjusting device 3 is connected to the guide bow 1 by a wing screw 89 (or an eccentric, a snap hood or the like). By means of this connection, the adjusting device 3 is pressed or pushed into the guide bow 1 so that the targeting device 5 is clamped or secured between the adjusting device 3 and the guide bow 1.

By means of this flap concept, it is exemplarily advantageously possible to replace the targeting device 5.

FIG. 25 shows a targeting device 5, which is movably arranged by means of a spring concept between the adjusting device 5 and the guide bow 1. In this embodiment, the targeting device 5 comprises two sections or shells, between which a spiral spring 91 is arranged. The upper section (with reference to FIG. 25) is pushed upward by the spiral spring 91. As a result, the protrusions 93 arranged on the upper side rest or snap into bores 95 (or grooves) on the bottom side of the adjusting device 5. For example, ten protrusions 93 and bores 95 may be arranged on the upper or bottom side, respectively.

FIG. 26 shows a further targeting device 5, which is movably arranged by means of a thread concept between the adjusting device 3 and the guide bow 1. By means of a thread 97, the upper shell of the targeting device 5 may be pressed against the bottom side of the adjusting device 3 and the bottom side of the lower shell of the targeting device 5 may be pressed and fixed against the upper side of the guide bow 1.

FIG. 27 shows a further embodiment of the positioning device 100''' according to the present invention.

A first section 1*a* (in FIG. 27) is connected to the sleeve guide 2, in particular releasably. Alternatively, the connection may be a non-releasable material-bonding connection, for example a solder connection, a welded connection or an adhesive connection. The material-bonding, integral connection, may be a one-piece component, e.g., made of a material which is made of casting and/or machining. The first section 1*a* may be produced by means of a generative production method, e.g., by means of a laser sintering method or a rapid prototyping method.

A second section 1*b* of the guide bow 1 may be produced as one part or multiple-part.

The first section 1*a* and the second section 1*b* may be connected, at an interface 101, to each other by means of a form-fit or. For example, the second section 1*b* may be form-fit or positively pushed in by means of a step into a hollow end section of the first section 1*a*. This form-fit connection may then be fixed and secured by means of one or several bolts 103 (the bolts 103 may be dowel pins). The form-fit or may be additionally secured by means of an adhesion. An adhesion may be advantageous in order to ensure a play-free connection even after prolonged use and multiple mechanical stresses. A play-free connection may be important for a therapeutic success of an exact positioning of intramedullary nails by the positioning device 100''' according to the present invention.

The mounting of the snap-in pin 39, the handpiece 71, the spiral spring 69 and the screw 99 with the guide bow 1 takes place as described in FIG. 13. In addition, in the embodiment in FIG. 27, a small pin 105 (the pin 105 may be referred to as pin) is fixed or connected to the snap-in pin 39. The spiral spring 69 and the pin 105 are designed such that the spiral spring 69 is usually first mechanically elastically deformed in order to allow it to be moved or pushed through the pin 105 on the snap-in pin 39. (In FIG. 27 the spiral spring 69 is moved to the left by pin 105 in the direction of the handpiece 71). In this way, the spiral spring 69 cannot separate independently from the snap-in pin 39 without renewed elastic deformation. This has the advantage that sterilization of the arrangement may be carried out without dismantling of the spiral spring 69.

The rotary tightener 67 connects and secures, in the mounted state, the targeting device 5 and the adjusting device 3 to the guide bow 1. The rotary tightener 67 is explained more closely in FIG. 31.

The targeting device 5 comprises concentric rings 109 on at least one surface (on the right side in FIG. 27). These purely optical rings serve the user to control or orient the current positioning of the targeting device 5, which is movable between the rotary tightener 67 and the adjusting device 3.

Furthermore, the targeting device 5 comprises a longitudinal slit 111 on the circumference of the centrical, sleeve-shaped protrusion. This longitudinal slit 111 serves to elastically deform the annular protrusion when inserting the instrument for inserting the interlocking screw 23 (see FIG. 11). In the non-deformed state, the inner diameter of the protrusion is slightly smaller than the diameter of the instrument 23. The protrusion is elastically deformed and expanded during the insertion of the instrument 23 and can subsequently be actively moved or rotated, by effort or force, against the frictional resistance between the protrusion and the instrument. Due to the frictional resistance, the instrument can only be actively moved, but cannot fall out or decouple. This type of clamping is advantageous when the instrument 23 cannot be permanently manually fixed and held, but still should remain in a predetermined position.

The second section 1b of the guide bow 1 comprises a positioning aid 27 as a bore for further instruments 23' (see FIG. 11) for inserting interlocking screws. This positioning aid 27 comprises also a longitudinal slit 113 (hidden) at one end (in FIG. 27 left), which has the same function as the longitudinal slit 111. Thus, an instrument 23' which is pushed into the bore of the positioning aid 27 is movable on the one hand, but is clamped on the other hand due to the frictional resistance to prevent it from falling out or decoupling.

Furthermore, the second section 1b comprises a bore 115 for a connecting pin, in particular for a dowel pin. By means of the dowel pin, the second section 1b can in particular be connected to an extension (not shown in FIG. 27) in order, for example, to provide further bores for positioning aids for inserting further interlocking screws into the intramedullary nail.

The components shown in FIG. 27 may be made of one or different materials. Preferably, the components of the second section 1b, the adjusting device 3, the targeting device 5 and the rotary tightener 67 are made of plastic; the remaining components are made of one or different metallic materials. By way of example, the plastic components may be made of, or comprise, one or different types of the following plastic: PEEK (polyetheretherketone); PEEK fiber reinforced; PEEK fiber reinforced in different concentrations of fibers; polyoxymethylene (POM); carbon fiber reinforced plastic (CFRP), polyarylsulfone, in particular polyphenylsulfone (PPSU). By way of example, the components made of metal are made of, or comprise, such a material. The stainless steel can be hardened and/or blasted.

FIG. 28 shows the sleeve 7 of FIG. 27 in a one-piece view. The longitudinal axis 11 of the sleeve 7 corresponds to the longitudinal axis of the intramedullary nail 19, which can be adapted and fixed at the left end (referring to FIG. 28) by means of a guiding device 9 (see FIG. 13). For controlling, e.g., the penetration depth of the intramedullary nail 19, a marking in millimeter is stamped on the sleeve.

Compared to the embodiment of the sleeve 7 in FIGS. 3 to 7, the sleeve 7 does not comprise a sliding guide 33.

FIG. 29 shows the sleeve 7 of FIG. 28 in a view rotated by 90 degrees about the longitudinal axis 11.

FIG. 30 shows the sleeve 7 in a half-section illustration A-A corresponding to the sectional plane shown in FIG. 29.

The guide bow 1 is positioned relative to the sleeve 7 by means of a snap-in pin 39, according to the mode of operation of the positioning device 100 already discussed above, for example in FIG. 10 and FIG. 15.

The positioning is exemplarily achieved here through the fact the snap-in pin 39 can be positioned in different bores 107 in the sleeve 7, and by means of this positioning an interlocking screw 21 is secured by means of an instrument 23 and a targeting device 5 in the intramedullary nail 19 and in the surrounding long bone.

The user of the positioning device 100 according to the present invention can thereby select between predetermined bores 107 which interlocking screw 21 he would like to position and secure in the intramedullary nail 19 and the long bone, respectively. With this selection, the snap-in pin 39 should, for example, possibly be moved only between the predetermined bores 107 in order to enable a fast and accurate fixing. To achieve this goal, the movement possibilities of the snap-in pin 39 are restricted by, for example, a milled area 119. The movement direction of the snap-in pin 39 along its longitudinal axis, illustrated by the arrow 121 in FIG. 28, is optionally limited, e.g. by stoppers, so that the snap-in pin 39 can preferably not be withdrawn over or beyond the outer diameter of the sleeve 7. The movement possibilities within the area 119 is clarified and illustrated in FIG. 28 by the gap 123.

In the mounted state of the positioning device 100, the bores 107 are optionally concealed by the sleeve guide 2 of the guide bow 1 In order to orient the user as to the actual position of the snap-in pin 39, markings 125, e.g. numbering, are preferably impressed or attached on the sleeve 7 in the non-concealed area. The markings correspond to the associated bores 107, respectively.

The area 119 in the embodiment of FIG. 28 to FIG. 30 is purely exemplarily. For example, it can be narrower and smaller in order to limit the possibilities of guiding the snap-in pin 39 and thus to enable or to select a faster and more precise positioning in a bore 107.

The bores 107 are optionally provided with chamfers in order to facilitate inserting the snap-in pin 39 into the bores 107. The bores 107 are preferably provided with clearances to allow a play-free positioning.

FIG. 31 shows a further rotary tightener 67. In this embodiment, the rotary tightener 67 has asymmetrical engagement contours or peripheral or external contours for, in particular manual, tightening and releasing.

The optional asymmetrical engagement contour of FIG. 31 may be referred to as a sawtooth contour. The rotary tightener 67 is, e.g., tightened in the clockwise direction (relative to the view in FIG. 31) of the direction of rotation 129 and is released counterclockwise. The flank in clockwise direction is much flatter than the flank for release. In this, only a small amount of torque can be applied. If the torque is increased too much, the hand or the fingers in contact slip beyond the nubs 131 during manual tightening by the user. In this way, it can advantageously be achieved that no too high torques may be applied for tightening the rotary tightener. Very high torques could cause damage or breaking of this component which is preferably made of plastic. Preferably, in the present embodiment, it is simpler to apply torque onto the rotary tightener for releasing than torque on it for tightening. The user can therefore be sure that he can also manually release the rotary tightener having been manually tightened by himself.

A tool can also be used alternatively to a pure manual actuation of the rotary tightener 67.

The different inclination of the flanks are defined by the radii 133 and 135. The radius 133 may be approximately 6 mm and the radius 135 may be approximately 49 mm, by way of example.

LIST OF REFERENCE NUMERALS 100, 100',
100", positioning device
100'''
x x-direction; movement direction of the adjusting device along the guide bow
y-direction; direction perpendicular to the movement direction of the adjusting device along the guide bow; in the circumferential direction of the sleeve
1 guide bow
1a first area or section of the guide bow
1b second area or section of the guide bow
2 sleeve guide
3 adjusting device
5 targeting device
7 sleeve
9 guiding device
11 longitudinal axis of the sleeve 13 circumferential direction of the sleeve
15, 15' snap-in arrangement
17 locking or retaining screw
19 intramedullary nail
21, 21' locking device, locking screw
23, 23' instrument for inserting the locking device or the interlocking screw
25 through-opening
27 positioning aid
28 inner thread
29 sliding guide
31 guide step or landing
33 groove-shaped extension of the sliding guide in the circumferential direction of the sleeve
35 snap-in position; long hole in the sleeve
37 marking for position control
39 snap-in pin; bolt of the snap-in arrangement
41 leaf spring
43 bolt arrangement
45 lever
47 gear connection
49 bar of the sleeve
51 thread
53 pin; supported in radial direction by a spring or in a springy manner
55 tool
57 connector
59 lever
60 movement direction of the lever; arrow direction
61 magnet
63 magnet
65 connection screw
67 rotary tensioner
69 spiral spring for snap-in pin
71 handpiece
73 leaf spring
75 lever
77 thread on the snap-in pin
79 thread of or for the two-piece targeting device
81 snap-in device
83 hole arrangement
85 locking or retaining screw
87 point-shaped or punctiform fixation
89 wing screw
91 spiral spring for targeting device
93 protrusion on the upper surface of the targeting device
95 bores or holes of the bottom side of the adjusting device
97 thread for targeting device
99 screw
101 interface between the first and the second section of the guide bow
103 bolt; dowel pin
105 pin
107 bores of the sleeve
109 concentric rings of the targeting device
111 longitudinal slit of the sleeve-shaped protrusion of the targeting device
113 longitudinal slit of the positioning aid
115 bore for dowel pin
117 marking in millimeters
119 range of movement by snap-in pin
121 movement direction of the snap-in pin
123 gap width for moving the snap-in pin
125 markings
127 chamfer
129 rotation direction of the rotating tightener
131 nubs
133 first radius of the rotating tightener
135 second radius of the rotating tightener

The invention claimed is:

1. A positioning device for positioning and/or securing an intramedullary nail in a long bone; comprising:
 a guide bow (1) which comprises or is connected to:
  an adjusting device (3), wherein the adjusting device (3) comprises at least a targeting device (5), and wherein the targeting device (5) is designed to at least partially receive a locking device (21) or an instrument (23) for acting on the locking device (21); and
  a sleeve guide (2) having a sleeve (7), wherein the sleeve (7) is mounted in the sleeve guide (2) such that it can be rotated and slid relative to the sleeve guide (2), and wherein the sleeve (7) comprises a longitudinal through-opening for receiving a guiding device (9),
 wherein the guide bow (1) is arranged to be displaceable along the longitudinal axis of the sleeve relative thereto and to be rotatable about the longitudinal axis of the sleeve relative thereto, and
 wherein the guide bow (1) is designed, at least in section, as a circular bow, and wherein the adjusting device (3) is arranged to be movable, at least in section, along the circular bow.

2. The positioning device (100, 100', 100") according to claim 1, further comprising a guiding device (9) inserted into the sleeve (7).

3. The positioning device (100, 100', 100") according to claim 1, wherein the sleeve (7) and/or the guiding device (9) comprises a connection section for releasably connecting it to an intramedullary nail (19).

4. The positioning device (100, 100', 100") according to claim 1, wherein the sleeve (7) comprises a sliding guide (29) for guiding a section, in particular a guide step (31), of the guide bow (1) or of the sleeve guide (2) along the sleeve (7) or vice versa.

5. The positioning (100, 100', 100") according to claim 1, wherein the guide bow (1) comprises a snap-in pin (39) being movable between at least two positions, and wherein the sleeve (7) comprises at least one snap-in position (35) for inserting or snapping-in the snap-in pin (39).

6. The positioning device ((100, 100', 100") according to claim 5, wherein the at least one snap-in position (35) comprises a longitudinal groove (33) being arranged in the/a circumferential direction (13) of the sleeve (7), wherein the longitudinal groove (33) allows moving the snap-in pin (39) in the circumferential direction (13) of the sleeve (7) when the snap-in pin (39) is in the at least one snap-in position (35).

7. The positioning device ((100, 100', 100") according to claim 1, wherein the sleeve (7) has markings (37) for controlling or monitoring the position of the guide bow (1) relative to the sleeve (7).

8. The positioning device (100, 100', 100") according to claim 1, wherein the guiding device (9) comprises an outer thread (51).

9. The positioning device (100, 100', 100") according to claim 8, wherein the guiding device (9) for guiding a tool (55) has a hollow interior, has a longitudinal opening and/or is tubular.

10. The positioning device (100, 100', 100") according to claim 1, wherein the adjusting device (3) is arranged to be movable in the longitudinal direction (x-direction) of the guide bow (1) together with the targeting device (3), which targeting device (3) is to be aligned with the intramedullary nail (19) during use of the positioning device (100, 100', 100'').

11. The positioning device (100, 100', 100'') according to claim 1, wherein the targeting device (5) comprises an opening (25) which faces the intramedullary nail (19) and which reaches through or passes through the adjusting device (3).

12. The positioning device (100, 100', 100'') according to claim 1, wherein the guide bow (1) has stops for limiting the displacement path of the adjusting device (3) along the circular bow.

13. The positioning device ((100, 100', 100'') according to claim 1, wherein the targeting device (5) is displaceable or movable in longitudinal direction (x-direction) of the guide bow (1) and in perpendicular direction (y-direction) to the longitudinal direction (x-direction) of the guide bow (1).

14. The positioning device (100, 100', 100'') according to claim 1, wherein the targeting device (5) is arranged in the adjusting device (3) and is displaceable relative thereto.

15. The positioning device (100, 100', 100'') according to claim 14, wherein the targeting device (5) is movably arranged at least in a first position for moving the targeting device (5) relative to the adjusting device (3) and is non-movably arranged at least in a second position for the releasable fixing of the targeting device (5) relative to the adjusting device (3).

16. The positioning device (100, 100', 100'') according to claim 1, releasably connected to an intramedullary nail (19).

17. A positioning device for positioning and/or securing an intramedullary nail in a long bone; comprising:
  a guide bow (1) which comprises or is connected to:
    an adjusting device (3), wherein the adjusting device (3) comprises at least a targeting device (5), and wherein the targeting device (5) is designed to at least partially receive a locking device (21) or an instrument (23) for acting on the locking device (21); and
    a sleeve guide (2) having a sleeve (7), wherein the sleeve (7) is mounted in the sleeve guide (2) such that it can be rotated and slid relative to the sleeve guide (2), and wherein the sleeve (7) comprises a longitudinal through-opening for receiving a guiding device (9),
  wherein the guide bow (1) is arranged to be displaceable along the longitudinal axis of the sleeve relative thereto and to be rotatable about the longitudinal axis of the sleeve relative thereto, and
  wherein the sleeve (7) comprises a sliding guide (29) for guiding a section, in particular a guide step (31), of the guide bow (1) or of the sleeve guide (2) along the sleeve (7) or vice versa.

18. The positioning (100, 100', 100'') according to claim 17, wherein the guide bow (1) comprises a snap-in pin (39) being movable between at least two positions, and wherein the sleeve (7) comprises at least one snap-in position (35) for inserting or snapping-in the snap-in pin (39).

19. The positioning device ((100, 100', 100'') according to claim 18, wherein the at least one snap-in position (35) comprises a longitudinal groove (33) being arranged in the/a circumferential direction (13) of the sleeve (7), wherein the longitudinal groove (33) allows moving the snap-in pin (39) in the circumferential direction (13) of the sleeve (7) when the snap-in pin (39) is in the at least one snap-in position (35).

20. A positioning device for positioning and/or securing an intramedullary nail in a long bone; comprising:
  a guide bow (1) which comprises or is connected to:
    an adjusting device (3), wherein the adjusting device (3) comprises at least a targeting device (5), and wherein the targeting device (5) is designed to at least partially receive a locking device (21) or an instrument (23) for acting on the locking device (21); and
    a sleeve guide (2) having a sleeve (7), wherein the sleeve (7) is mounted in the sleeve guide (2) such that it can be rotated and slid relative to the sleeve guide (2), and wherein the sleeve (7) comprises a longitudinal through-opening for receiving a guiding device (9),
  wherein the guide bow (1) is arranged to be displaceable along the longitudinal axis of the sleeve relative thereto and to be rotatable about the longitudinal axis of the sleeve relative thereto, and
  wherein the guide bow (1) is designed, at least in section, as a circular bow, and has stops for limiting the displacement path of the adjusting device (3) along the circular bow.

* * * * *